United States Patent [19]

Weinhardt et al.

[11] Patent Number: 5,739,336

[45] Date of Patent: Apr. 14, 1998

[54] 1,3,8-TRIAZA- AND 3,8-DIAZA-1-OXASPIRO [4,5] DECANE DERIVATIVES

[75] Inventors: Klaus K. Weinhardt, Palo Alto; Jacob Berger, Los Altos Hills; David S. Carter, Costa Mesa; Lee A. Flippin, Woodside, all of Calif.

[73] Assignee: Syntex (U.S.A.) Inc., Palo Alto, Calif.

[21] Appl. No.: 667,247

[22] Filed: Jun. 20, 1996

Related U.S. Application Data

[60] Provisional application No. 60/035,193 Jun. 23, 1995.

[51] Int. Cl.[6] ............ A61K 31/395; C07D 471/10
[52] U.S. Cl. ............ 546/20; 546/19; 514/278; 549/430
[58] Field of Search ............ 546/20, 19

[56] References Cited

U.S. PATENT DOCUMENTS

| 3,155,669 | 11/1964 | Janssen | 260/294 |
| 3,155,670 | 11/1964 | Janssen | 260/294 |
| 3,161,644 | 12/1964 | Janssen | 260/293 |
| 3,594,386 | 7/1971 | Regnier et al. | 260/293.4 |
| 5,143,938 | 9/1992 | Calvet et al. | 514/653 |
| 5,236,947 | 8/1993 | Calvet et al. | 514/433 |

FOREIGN PATENT DOCUMENTS

0450995A1 10/1991 European Pat. Off. ...... C07D 37/28
1815450 12/1967 Germany ...... 260/293.4
48-34597 10/1973 Japan.

OTHER PUBLICATIONS

Sasajima et al. "Chem Pharm Bull" vol. 28, No. 8, pp. 2502–2507 (1978).

G. Winters et al., "Sintesi di spiroidantoine da chetoni eterociclici basici", *Il Farmaco—Ed. Sc.*, 25(9), 681–693 (1970).

*Primary Examiner*—Robert T. Bond
*Attorney, Agent, or Firm*—Heller Ehrman White & McAuliffe

[57] ABSTRACT

Heterocyclic compounds of Formula I:

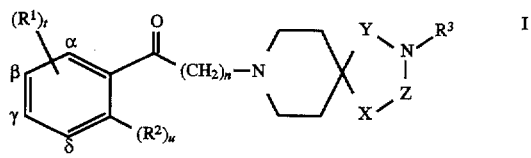

in which n is 2, 3, 4, 5 or 6; t is 1, 2, 3 or 4; u is 0 or 1 (provided that t is not 1 when u is 0); X is O or $N(R^4)$; Y and Z are independently C(O), C(S) or $CH_2$ (provided that Y and Z are not both $CH_2$); $R^1$, $R^2$, $R^3$, and $R^4$ are as defined in the specification; and their pharmaceutically acceptable salts and N-oxides, formulations containing them, their uses as therapeutic agents, and their synthesis.

17 Claims, No Drawings

1,3,8-TRIAZA- AND 3,8-DIAZA-1-OXASPIRO [4,5] DECANE DERIVATIVES

CROSS-REFERENCE TO RELATED APPLICATION

This application claims the benefit under 35 U.S.C. 119(e) of U.S. Provisional application Ser. No. 60/035,193, filed Jun.23, 1995.

FIELD OF THE INVENTION

This invention relates to 1,3,8-triaza- and 3,8-diaza-1-oxaspiro[4.5]decane derivatives, their formulations and uses as therapeutic agents, and their synthesis.

BACKGROUND OF THE INVENTION

Serotonin, a neurotransmitter with mixed and complex pharmacological characteristics, was first discovered in 1948 and subsequently has been the subject of substantial research. Serotonin, also referred to as 5-hydroxytryptamine (5-HT), acts both centrally and peripherally on discrete 5-HT receptors. The 5-HT receptor is presently delineated into four major subclassifications 5-HT$_1$, 5-HT$_2$, 5-HT$_3$ and 5-HT$_4$ receptors—of which the 5-HT$_1$ and 5-HT$_2$ subtypes are also heterogeneous.

The 5-HT$_{2C}$ receptor, first characterized as a 5-HT$_{1C}$ subtype (see Pazos et al. (1984), Eur. J. Pharmacol., 106, 539-546) and subsequently recognized as belonging to the 5-HT$_2$ receptor family (see Pritchett et al. (1988), *EMBO J.*, 7, 4135–4140), is widely distributed in the human brain (see Pazos et al. (1987), *Neuroscience*, 21, 97–122). Current evidence strongly supports a therapeutic role for 5-HT$_{2C}$ receptor antagonists in treating anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism (see Kennett (1993). *Curr. Opin. Invest. Drugs*, 2, 317–362). Support for these therapeutic indications rests in the clinical and experimental pharmacology reported for 1-(3-chlorophenyl)piperazine [mCPP, a 5-HT$_{2C}$ receptor agonists, non-selective 5-HT$_{2C/2A}$ receptor antagonists and selective 5-HT$_{2A}$ receptor antagonists (see Kennett (1993i, supra.; and Kennett et al. (1994), *Br. J. Pharmacol.*, 111, 797–802). Further evidence of the therapeutic applications of 5-HT$_{2C}$ receptor antagonists are findings that 5-HT reuptake inhibitors, the current therapy of choice for obsessive compulsive disorder, alcoholism and depression and becoming more widely accepted in treating panic disorder and migraine, exert their therapeutic efficacy after chronic administration and subsequent alteration (desensitization) of the 5-HT$_{2C}$ receptor. Thus, selective 5-HT$_{2C}$ receptor antagonists will offer distinct therapeutic advantages collectively in efficacy, rapidity of onset and absence of side effects (see Kennett (1993), supra.).

Current evidence also supports a therapeutic role for 5-HT$_2$ receptor antagonists in the treatment of both Parkinson's disease and the drug-induced psychosis or dyskinesia found in some Parkinson's disease patients treated with antiparkinsonian drugs such as L-DOPA, carbidopa, bromocriptine, trihexyphenidyl, and amantadine (see Ikeguchi et al. (1995), *Eur. Arch. Psych. Clin. Neuroscience*, 244, 320–324; Bonifati et al. (1994), *Clin. Neuropharm.*, 17, 73–82; Henderson et al. (1992), *Clin. Exp. Neurology*, 29, 277–282). Thus, selective 5-HT$_{2C}$ receptor antagonists will offer distinct therapeutic advantages in the treatment of both Parkinson's disease and antiparkinsonian-drug-induced psychosis or dyskinesia.

The disclosures of these and other documents referred to throughout this application (e.g., in the Pharmacology section of the Detailed Description of the Invention) are incorporated herein by reference.

SUMMARY OF THE INVENTION

A first aspect of this invention is compounds of Formula I:

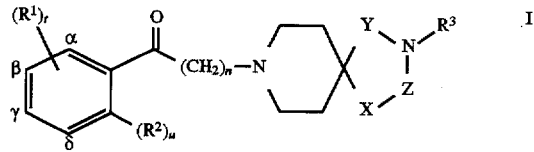

in which:

n is 2, 3, 4, 5 or 6;

t is 1, 2, 3 or 4 and u is 0 or 1 (provided that t is not 1 when u is 0);

X is O or N(R$^4$);

Y and Z are independently C(O), C(S) or CH$_2$ (provided that Y and Z are not both CH$_2$; and preferably where Y is C(O) and Z is C(O) or C(S)); each R$^1$ is independently amino, aryloxy, aryl (C$_{1-4}$)alkyloxy, arylsulfonyl, arylthio, carbamoyl, cyano, halo, nitro, thiocarbamoyl, thioureido, ureido, a group selected from (C$_{1-4}$)alkyl, (C$_{1-4}$)alkyloxy and (C$_{1-4}$)alkylthio (optionally further substituted with one to three halo atoms), a group selected from —NHSO$_2$R$^5$, —NHC(O)R$^5$, —NHC(O)NHR$^5$, —NHC(S)NHR$^5$ and —SO$_2$NHR$^5$ {which R$^5$ is (C$_{1-4}$)alkyl (optionally further substituted with one to three halo atoms) or a group selected from aryl, aryl (C$_{1-4}$)alkyl, heteroaryl and heteroaryl (C$_{1-4}$)alkyl (optionally further substituted with one to two radicals independently selected from amino, carbamoyl, cyano, halo, nitro, a group selected from (C$_{1-4}$)alkanoyl, (C$_{1-4}$)alkyl sulfonylamino, (C$_{1-4}$) alkanoylamino, (C$_{1-4}$)alkyl and (C$_{1-4}$)alkyloxy, optionally further substituted with one to three halo atoms, and a group selected from aryl, arylsulfonyl, heteroaryl and heteroarylsulfonyl, optionally further substituted with one to two radicals independently selected from amino, cyano, halo, nitro and a group selected from (C$_{1-4}$)alkyl and (C$_{1-4}$)alkyloxy, optionally further substituted with one to three halo atoms)} or with an adjacent R$^1$ radical form ethylenedioxy, methylenedioxy or butadienylene (which butadienylene is optionally further substituted with one to two radicals selected from halo and (C$_{1-4}$)alkyloxy);

R$^2$ is hydroxy, halo, (C$_{1-4}$)alkyloxy or aryl (C$_{1-4}$) alkyloxy;

R$^3$ is hydro, (C$_{1-6}$)alkyl (optionally substituted with a group selected from —C(O)OH, —C(O)O(C$_{1-4}$)alkyl, —NHSO$_2$R$^5$ and —NHC(O)R$^5$, in which R$^5$ is as defined above), hydroxyalkyl, esterified hydroxyalkyl, —CH$_2$O(C$_{1-4}$)alkyl, —CH$_2$OC(O)(C$_{1-4}$)alkyl, phenyl (C$_{1-4}$)alkyl (optionally substituted with one or two radicals independently selected from amino, cyano, halo, hydroxy, nitro, trifluoromethyl, trifluoromethoxy, acetamido, methanesulfonamido, (C$_{1-4}$)alkyl, or (C$_{1-4}$) alkyloxy), or a group of Formula (a):

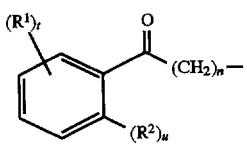

in which each n, t and $R^1$ are as defined above with respect to Formula I; and $R^4$ is hydro, $(C_{1-4})$alkyl, or aryl, or $R^4$ and $R^3$ are the same and are —$CH_2O(C_{1-4})$alkyl or —$CH_2OC(O)(C_{1-4})$alkyl;

and the pharmaceutically acceptable salts and N-oxides thereof.

A second aspect of this invention is pharmaceutical compositions which contain one or more compounds of Formula I in admixture with one or more suitable excipients.

A third aspect of this invention is methods for treating diseases capable of amelioration by administration of a 5-$HT_{2C}$ receptor antagonist, which method comprises administering to such animal a therapeutically effective amount of a compound of Formula I or a pharmaceutically acceptable salt or salts thereof.

A fourth aspect of this invention is the processes for preparing compounds of Formula I and is set forth in "Detailed Description of the Invention".

DETAILED DESCRIPTION OF THE INVENTION

DEFINITIONS:

Unless otherwise stated, the following terms used in the specification and claims have the meanings given below:

"Aryl", as in aryl, aryl$(C_{1-4})$alkyl, aryl$(C_{1-4})$alkyloxy, aryloxy, arylsulfonyl and arylthio means a radical derived from an aromatic hydrocarbon containing 6 to 14 ring carbon atoms and includes monocyclic or condensed carbocyclic aromatic rings (e.g., phenyl, naphthyl, anthracenyl, phenanthrenyl, etc.) optionally substituted with one or more radicals.

"Alkyl", as in $(C_{1-6})$alkyl, $(C_{1-6})$alkyloxy and $(C_{1-4})$alkylthio, means a straight or branched saturated hydrocarbon radical having from one to the number of carbon atoms designated optionally substituted with one to three halo atoms (e.g., optionally substituted $(C_{1-4})$alkylthio includes methylthio, ethylthio, 2,2,2-trifluoroethylthio, etc.; optionally substituted $(C_{1-6})$alkyl includes methyl, trifluoromethyl, ethyl, propyl, isopropyl, butyl, isobutyl, sec-butyl, tert-butyl, etc.; and optionally substituted $(C_{1-6})$alkyloxy includes methoxy, difluoromethoxy, trifluoromethoxy, ethoxy, 2,2,2-trifluoroethoxy, propoxy, isopropoxy, butoxy, isobutoxy, sec-butoxy, tert-butoxy, etc.).

"Hydroxyalkyl" means a straight or branched monovalent hydrocarbon radical of two to four carbons substituted with one or two hydroxy groups, provided that: (1) the carbon bonded to the nitrogen is unsubstituted with hydroxy, and (2) if two hydroxy groups are present, they are not both on the same carbon atom. Examples include 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl, and 2-(hydroxymethyl)-3-hydroxypropyl.

"Esterified hydroxyalkyl" means a hydroxyalkyl radical as defined in the previous paragraph in which the hydroxy group (if only one is present) or both hydroxy groups (if two are present) are esterified with a $(C_{1-4})$alkanoic acid, such as acetic acid, propanoic acid, etc., or, preferably, with a neutral naturally occurring α-amino acid, such as glycine, alanine, valine, leucine, isoleucine, proline, etc. The amino acid may be in the D-, L-, or D,L-form; preferably in the L-form; and preferred amino acids are L-alanine, L-valine, L-leucine, and L-isoleucine. Exemplary esterified hydroxyalkyl radicals are 2-propionyloxyethyl, 2,3-diacetoxypropyl, 3-L-valyloxypropyl, and the like.

"Alkanoyl" means the radical —C(O)R, in which R is H or alkyl as the term is defined above (e.g., the term $(C_{1-4})$alkanoyl includes formyl, acetyl, propionyl, and butyryl).

"Carbamoyl" means aminocarbonyl.

"Halo" means fluoro, chloro, bromo, or iodo.

"Heteroaryl", as in heteroaryl, heteroaryl $(C_{1-4})$alkyl, heteroaryloxy, heteroaryl $(C_{1-4})$alkyloxy and heteroarylsulfonyl, means a radical derived from an aromatic hydrocarbon containing 5 to 14 ring carbon atoms, 1 to 5 of which are substituted by hetero atoms chosen from N, O, or S, and includes monocyclic, condensed heterocyclic and condensed carbocyclic and heterocyclic aromatic rings (e.g., thienyl, furyl, pyrrolyl, pyrimidinyl, isoxazolyl, oxazolyl, indolyl, benzo[b]thienyl, isobenzofuranyl, purinyl, isoquinolyl, pteridinyl, imidazolyl, pyridyl, pyrazolyl, pyrazinyl, quinolyl, etc.) optionally substituted with one to two radicals independently selected from halo and cyano.

"Sulfamoyl" means the radical aminosulfonyl.

"Thiocarbamoyl" means the radical —C(S)$NH_2$—.

"Thioureido" means the radical —NHC(S)$NH_2$.

"Leaving group" has the meaning conventionally associated with it in synthetic organic chemistry, i.e., an atom or group displaceable under alkylating conditions, and includes halogen and alkane- or arenesulfonyloxy, such as mesyloxy, ethanesulfonyloxy, benzenesulfonyloxy and tosyloxy, and thienyloxy, dihalophosphinoyloxy, tetrahalophosphaoxy, and the like.

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Optional" or "optionally" means that the subsequently described event or circumstance may or may not occur, and that the description includes instances where the event or circumstance occurs and instances in which it does not. For example, the phrase "optionally further substituted with one to three halo atoms" means that the group referred to may or may not be substituted in order to fall within the scope of the invention.

"Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed.

"Protecting agent" means an agent which will react with a multifunctional compound and create a protective group at reactive nitrogen atoms.

"Protected" in reference to a compound or a group means a derivative of compound or group in which a reactive site or sites are blocked with protective groups.

"Deprotecting" refers to removing any protective groups present after the selective reaction has been carried out.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrobromic acid, hydrochloric acid, nitric acid, phosphoric acid, sulfuric acid and the like; or with organic acids such as acetic acid, benzenesulfonic acid, benzoic acid, camphorsulfonic acid, p-chlorobenzenesulfonic acid, cinnamic acid, citric acid, cyclopentanepropionic acid, 1,2-ethanedisulfonic acid, ethanesulfonic acid, fumaric acid, glucoheptonic acid, gluconic acid, glutamic acid, glycolic acid, hexanoic acid, heptanoic acid, o-(4-hydroxybenzoyl) benzoic acid, 2-hydroxyethanesulfonic acid, hydroxynaphthoic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trimethylacetic acid and the like.

Pharmaceutically acceptable salts also include salts which may be formed when acidic protons present are capable of reacting with inorganic or organic bases. Acceptable inorganic bases include aluminum hydroxide, calcium hydroxide, potassium hydroxide, sodium carbonate and sodium hydroxide. Acceptable organic bases include diethanolamine, ethanolamine, N-methylglucamine, triethanolamine, tromethamine, and the like.

"N-Oxide", when referring to a compound of Formula I, means such compound in which nitrogens are in an oxidized state, i.e., O←N. The N-oxides of compounds of Formula I can be prepared by methods known to those of ordinary skill in the art.

"Therapeutically effective amount" means that amount which, when administered to an animal for treating a disease, is sufficient to effect such treatment for the disease.

The term "q.s." means adding a quantity sufficient to achieve a stated function, e.g., to bring a solution to the desired volume (i.e., 100%).

"Treating" or "treatment" of a disease includes:
(1) preventing the disease from occurring in an animal which may be predisposed to the disease but does not yet experience or display symptoms of the disease,
(2) inhibiting the disease, i.e., arresting its development, or
(3) relieving the disease, i.e., causing regression Of the disease.

For the purposes of this application the term "α-position" in reference to a compound of Formula I, 3 or 6–17 means that position on the phenyl group of the benzoyl moiety which is adjacent to the position at which the carbonyl carbon, or a protected derivative thereof, is attached. A reference to "β-, γ- or δ-position" means that position on the phenyl group as it would traditionally relate to the α-position.

"Adjacent" as in the term "with an adjacent $R^1$ radical form ethylenedioxy, methylenedioxy or butadienylene" means that two $R^1$ radicals are at adjacent positions on the phenyl ring and together form a bivalent radical (e.g., α,β-butadienylene, β,γ-butadienylene, γ,δ-butadienylene, β,γ-methylenedioxide, α,β-ethylenedioxide, etc.).

The compounds of Formula I are named by AUTONOM Version 1.0 by Beilstein-Institut and Springer-Verlag Berlin Heidelberg, a fully automatic computerized system for assigning IUPAC systematic nomenclature directly from the structural diagrams of organic compounds. For example, a compound of the following formula:

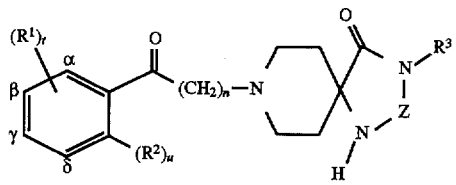

is named N-{5-[5-(2,4-dioxo-1,3,8-triazaspiro[4.5]dec-8-yl)pentanoyl]-2,4-dimethoxyphenyl}benzenesulfonamide when n is 4, t is 2, u is 1, Z is C(O), $R^1$ is phenylsulfonylamino and methoxy at the β- and γ-positions, respectively, $R^2$ is methoxy and $R^3$ is hydro;

is named 8-[5-(2,3-ethylenedioxyphenyl)-5-oxopentyl]-1,3,8-triazaspiro[4.5]decane-2,4-dione when n is 4, t is 2, u is 0, Z is C(O), $R^1$ is α,β-ethylenedioxy and $R^3$ is hydro; and is named N-(2-{8-[4-(2,4-dimethoxyphenyl)-4-oxobutyl]-1,3,8-triaza-2,4-dioxospiro[4.5]dec-3-yl}ethyl) methanesulfonamide when n is 3, t is 1, u is 1, $R^1$ is methoxy at the γ-position, $R^2$ is methoxy and $R^3$ is 2-(methylsulfonylamino) ethyl.

PRESENTLY PREFERRED EMBODIMENTS:

While the broadest definition of this invention is set forth in the Summary of the Invention, certain compounds of Formula I are preferred.

For example, preferred compounds of Formula I are those in which n is 3, 4, 5 or 6; u is 0; X is NH; Y is C(O); Z is C(O) or C(S); two adjacent $R^1$ radicals form α,β-ethylenedioxy; a third $R^1$ radical, when present, is amino, phenyl, phenoxy, halo, nitro, ureido, thioureido, $(C_{1-4})$alkyloxy, a group selected from —NHSO$_2$R$^5$, —NHC(O)R$^5$, —NHC(O)NHR$^5$ and —NHC(S)NHR$^5$ {which R$^5$ is $(C_{1-4})$alkyl or a group selected from phenyl, naphthyl and thienyl (optionally further substituted with one to two radicals independently selected from amino, carbamoyl, cyano, halo, nitro, a group selected from $(C_{1-4})$alkanoyl, $(C_{1-4})$alkylsulfonylamino, $(C_{1-4})$alkanoylamino, $(C_{1-4})$alkyl and $(C_{1-4})$alkyloxy, optionally further substituted with one to three halo atoms, and a group selected from aryl, arylsulfonyl, heteroaryl and heteroarylsulfonyl, optionally further substituted with one to two radicals independently selected from amino, cyano, halo, nitro and a group selected from $(C_{1-4})$alkyl and $(C_{1-4})$alkyloxy, optionally further substituted with one to three halo atoms)}; and $R^3$ is hydro, $(C_{1-6})$alkyl (optionally substituted with a group selected from —C(O)OH, —C(O)O$(C_{1-4})$alkyl, —NHSO$_2$R$^5$ and —NHC(O)R$^5$, in which R$^5$ is as defined above), hydroxyalkyl, esterified hydroxyalkyl, or phenyl $(C_{1-4})$alkyl (optionally substituted with one or two radicals independently selected from amino, cyano, halo, hydroxy, nitro, trifluoromethyl, trifluoromethoxy, acetamido, methanesulfonamido, $(C_{1-4})$alkyl, or $(C_{1-4})$alkyloxy).

Other preferred compounds of Formula I are those in which n is 3, 4, 5 or 6; X is NH; Y is C(O); Z is C(O) or C(S); u is 1; t is 1, 2 or 3; $R^1$ is amino, phenyl, phenoxy, halo, nitro, ureido, thioureido, $(C_{1-4})$alkyloxy, a group selected from —NHSO$_2$R$^5$, —NHC(O)NHR$^5$, —NHC(O)NHR$^5$ and —NHC(S)NHR$^5$ {which R$^5$ is $(C_{1-4})$alkyl or a group selected from phenyl, naphthyl, thienyl (optionally further substituted with one to two radicals independently selected from amino, carbamoyl, cyano, halo, nitro, a group selected from ($C_{1-4}$)alkanoyl, ($C_{1-4}$)alkylsulfonylamino, ($C_{1-4}$)alkanoylamino, ($C_{1-4}$)alkyl and ($C_{1-4}$)alkyloxy, optionally further substituted with one to three halo atoms, and a group selected from aryl, arylsulfonyl, heteroaryl and heteroarylsulfonyl, optionally further substituted with one to two radicals independently selected from amino, cyano, halo, nitro and a group selected from ($C_{1-4}$)alkyl and ($C_{1-4}$)alkyloxy, optionally further substituted with one to three halo atoms)} or with an adjacent $R^1$ radical form butadienylene (which butadienylene is optionally further substituted with one to two radicals selected from halo and ($C_{1-4}$)alkyloxy); $R^2$ is ($C_{1-4}$)alkyloxy; and $R^3$ is hydro, ($C_{1-6}$)alkyl (optionally substituted with a group selected from —C(O)OH, —C(O)O($C_{1-4}$)alkyl, —NHSO$_2$R$^5$ and —NHC(O)R$^5$, in which R$^5$ is as defined above), hydroxyalkyl, esterified hydroxyalkyl, or phenyl ($C_{1-4}$)alkyl (optionally substituted with one or two radicals independently selected from amino, cyano, halo, hydroxy, nitro, trifluoromethyl, trifluoromethoxy, acetamido, methanesulfonamido, ($C_{1-4}$)alkyl, or ($C_{1-4}$)alkyloxy).

Particularly preferred are those compounds of Formula I in which n is 4, 5 or 6; X is NH; Y is C(O); Z is C(O) or C(S); u is 1; t is 1, 2, or 3; an $R^1$ radical is attached at the β- and/or γ-positions, which $R^1$ radical when attached at the β-position is amino, phenoxy, chloro, nitro, ($C_{1-4}$)alkyloxy or —NHSO$_2$R$^5$ {which R$^5$ is a group selected from phenyl or thienyl (optionally further substituted with one to two radicals independently selected from amino, carbamoyl, cyano, halo, nitro, a group selected from ($C_{1-4}$)alkanoyl, ($C_{1-4}$) alkylsulfonylamino, ($C_{1-4}$)alkanoylamino, ($C_{1-4}$)alkyl and ($C_{1-4}$)alkyloxy, optionally further substituted with one to three halo atoms, and a group selected from aryl, arylsulfonyl, heteroaryl and heteroarylsulfonyl, optionally further substituted with one to two radicals independently selected from amino, cyano, halo, nitro and a group selected from ($C_{1-4}$)alkyl and ($C_{1-4}$)alkyloxy, optionally further substituted with one to three halo atoms)} and when attached at the γ-position is chloro, ($C_{1-4}$)alkyloxy or amino.; $R^3$ is methoxy; and $R^3$ is hydro, ($C_{1-6}$)alkyl (optionally substituted with a group selected from —C(O)OH, —C(O)O ($C_{1-4}$)alkyl, —NHSO$_2$R$^5$ and —NHC(O)R$^5$, in which R$^5$ is as defined above), hydroxyalkyl, esterified hydroxyalkyl, or phenyl ($C_{1-4}$)alkyl (optionally substituted with one or two radicals independently selected from amino, cyano, halo, hydroxy, nitro, trifluoromethyl, trifluoromethoxy, acetamido, methanesulfonamido, ($C_{1-4}$)alkyl, or ($C_{1-4}$) alkyloxy).

Most preferred are those compounds of Formula I in which n is 4; X is NH; Y is C(O); Z is C(O); u is 1; t is 2 or 3; a first $R^1$ radical is attached at the β-position and is phenylsulfonylamino (optionally further substituted with amino, carbamoyl, cyano, chloro, fluoro, nitro or a group selected from ($C_{1-4}$)alkanoyl, ($C_{1-4}$)alkylsulfonylamino, ($C_{1-4}$)alkanoylamino, ($C_{1-4}$)alkyl and ($C_{1-4}$)alkyloxy, optionally further substituted with one to three fluoro atoms), a second $R^1$ radical is attached at the γ-position and is methoxy, the third $R^1$ radical if present is attached at the α-position and is methoxy; $R^3$ is methoxy; and $R^3$ is hydro, ($C_{1-6}$)alkyl, hydroxyalkyl, esterified hydroxyalkyl, or phenyl ($C_{1-4}$)alkyl {where the phenyl is optionally substituted halo, hydroxy, ($C_{1-4}$)alkyloxy, or trifluoromethyl}.

PHARMACOLOGY AND UTILITY:

The compounds of this invention are selective 5-HT$_{2C}$ receptor antagonists. Affinities for the 5-HT$_{2C}$ receptor were measured by a cloned rat 5-HT$_{2C}$ receptor binding assay (for details see Example 30, infra.). Antagonist properties were determined in NIH3T3 cells, transfected with cloned rat 5-HT$_{2C}$ receptor, by measuring the propensity of the compounds to inhibit 5-HT induced/5-HT$_{2C}$ mediated increases in cellular metabolic activity (for further details see Example 31, infra.). Accordingly, the compounds of this invention are useful for treating diseases which can be ameliorated by blocking 5-HT$_{2C}$ receptors. For example, clinical and experimental evidence support a therapeutic role for 5-HT$_{2C}$ receptor antagonists in treating anxiety. The 5-HT$_{2C}$ receptor agonist 1-(3-chlorophenyl)piperazine [mCPP] when administered to human volunteers causes anxiety (see Charney'et al. (1987), Psychopharmacology, 92, 14–24). mCPP also produces anxiogenic effects in rat, social interaction (SI) and elevated X-maze models of anxiety, which effects are blocked by non-selective 5-HT$_{2C/2A}$ receptor antagonists but not by selective 5-HT$_{2A}$ receptor antagonists (see Kennett et al. (1989), Eur. J. Pharmacol., 164, 445–454 and Kennett (1993), supra.). In addition, non-selective 5-HT$_{2C/2A}$ receptor antagonists by themselves produce anxiolytic effects in the SI and Geller Seifter conflict tests, while selective 5-HT$_{2A}$ receptor antagonists do not share this property.

Furthermore, mCPP when administered to panic disorder patients or obsessive compulsive disorder patients increases levels of panic and/or anxiety (see Charney et al. (1987), supra., and Zohar et al. (1987), Arch. Gen. Psychiat., 44, 946–951). Thus, current evidence support the application of selective 5-HT$_{2C}$ receptor antagonists for treating generalized anxiety disorder, panic disorder and obsessive compulsive disorder.

Anxiolytic activity can be determined experimentally by the art-recognized Crawley and Goodwin two-compartment exploratory model (e.g., see Kilfoil et al. (1989), Neuropharmacology, 28(9), 901–905). In brief, the method measures the extent a compound affects the natural anxiety of mice in a novel, brightly lighted area (for further details see Example 32, infra.).

Clinical and experimental evidence support a therapeutic role for selective 5-HT$_{2C}$ receptor antagonists in treating chemical dependency. The 5-HT$_{2C}$ receptor agonist mCPP induces a craving for alcohol in abstaining alcoholics (see Benkelfat et al. (1991), Arch. Gen. Psychiat., 48, 383). In contrast, the non-selective 5-HT$_{2C/2A}$ receptor antagonist ritanserin reduces alcohol preference in rats (see Meert et al., (1991), Drug Development Res. 24, 235–249), while the selective 5-HT$_{2A}$ receptor antagonist ketanserin has no affect on preference for alcohol (see Kennett et al., (1992), J. Psychopharmacol., Abstr. A26). Ritanserin also reduces both cocaine and fentanyl preference in rat models of addiction (see Meert et al. (1991), Drug Development Res. 25, 39–53 and Meert et al., (1991), Drug Development Res. 25, 55–66). Clinical studies show that ritanserin decreases alcohol intake in chronic alcoholics (see Monti et al. (1991), Lancet, 337, 60) and is useful in patients withdrawing from other drugs of abuse (see Sadzot et al. (1989), Psychopharmacology, 98, 495–499). Thus, current evidence support the application of selective 5-HT$_{2C}$ receptor antagonists for treating alcoholism and addiction to other drugs of abuse.

Ameliorating effects of compounds during withdrawal from drugs of abuse can be determined experimentally by the mouse, withdrawal anxiety test, an accepted assay (e.g., see Carboni et al. (1988), Eur. J. Pharmacol, 151, 159–160). This procedure utilizes the exploratory model described above to measure the extent a compound ameliorates the symptoms of withdrawal that occur after chronically treating with an addictive substance and then abruptly ceasing the treatments (for further details see Example 33, infra.).

Clinical evidence support a therapeutic role for selective 5-HT$_{2C}$ receptor antagonists in treating depression. For example., non-selective 5-HT$_{2C/2A}$ receptor antagonists show clinical efficacy in treating depression (see Murphy (1978), Brit. J. Pharmacol., 5, 81S–85S; Klieser et al. (1988), Pharmacopsychiat., 21, 391–393; and Camara (1991), Biol. Psychiat., 29, 201A). Furthermore, experimental results suggest that the mechanism by which conventional antidepressant drugs exert their therapeutic efficacy is through adaptive changes in the serotonergic system (see Anderson (1983), Life Sci., 32, 1791–1801). For example, chronic treatment with monamine oxidase inhibitors reduce mCPP-induced/5-HT$_{2C}$ mediated functional responses in a variety of paradigms. Similar effects are exhibited by selective 5-HT reuptake inhibitors. These findings suggest that treatments which enhance extraneuronal 5-HT levels desensitize 5-HT$_{2C}$ receptor function which in turn causes, or contributes to, antidepressant activity (see Kennett (1993), supra.).

Clinical evidence support a therapeutic role for selective 5-HT$_{2C}$ receptor antagonists in treating migraine. The 5-HT$_{2C}$ receptor agonist mCPP when administered to human volunteers causes migraine-like headaches. In contrast, non-selective 5-HT$_{2C/2A}$ receptor antagonists are clinically effective antimigraine agents, while the selective 5-HT$_{2A}$ receptor antagonist ketanserin is not (see Winther (1985), Cephalalgia, 5, 402–403). Furthermore, experimental results suggest that the clinical efficacy of chronic administration of 5-HT reuptake inhibitors as migraine prophylactics is due to desensitization of 5-HT$_{2C}$ receptors (see Kennett (1993), supra., and the above discussion on 5-HT$_{2C}$receptor desensitization and depression).

Clinical evidence support a therapeutic role for 5-HT$_{2C}$ receptor antagonists in treating sleep disorders. The 5-HT$_{2C}$ receptor agonist mCPP when administered to human volunteers reduces total sleep time, sleep efficiency, slow wave sleep (SWS) and rapid eye movement sleep (see Lawlor et al. (1991), Biol. Psychiat., 29, 281–286). In contrast, the non-selective 5-HT$_{2C/2A}$ receptor antagonist ritanserin increases SWS, reduces sleep onset latency and improves subjective sleep quality in healthy volunteers (see Idzikowski et al. (1986), Brain Res., 378, 164–168; Idzikowski et al. (1987), Psychopharmacology, 93, 416–420; Declerck et al. (1987), Curr. Therap. Res., 41, 427–432; and Adam et al. (1989), Psychopharmacology, 99, 219–221). Thus, given the opposing effects of 5-HT$_{2C}$ receptor stimulation and 5-HT$_{2C}$ receptor antagonism, selective 5-HT$_{2C}$ receptor antagonists could be of particular therapeutic value in treating sleep disorder (see Kennett (1993), supra.).

Clinical evidence support a therapeutic role for 5-HT$_{2C}$ receptor antagonists in feeding disorders. Non-specific 5-HT$_{2C/2A}$ receptor antagonists are shown to produce increased appetite and weight gain. Thus, there is some clinical evidence to support the application of selective 5-HT$_{2C}$ receptor antagonists for the treatment of anorexia nervosa.

Experimental evidence support a therapeutic role for 5-HT$_{2C}$ receptor antagonists in treating priapism. mCPP produces penile erections in rats, an effect that is blocked by non-selective 5-HT$_{2C/2A}$ receptor antagonists but not by selective 5-HT$_{2A}$ receptor antagonists (see Hoyer (1989), In: Fozard J. (ed.) Peripheral actions of 5-HT, Oxford University Press, Oxford, 72–99).

ADMINISTRATION AND PHARMACEUTICAL COMPOSITION:

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from 0.1 micrograms per kilogram body weight (μg/kg) per day to 1 milligram per kilogram body weight (mg/kg) per day, typically 1 μg/kg/day to 10 μg/kg/day. Therefore, a therapeutically effective amount for a 80 kg human may range from 8 μg/day to 800 mg/day, typically 80 μg/day to 0.8 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or Subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin. (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of Formula I in aerosol form. Inert gases suitable for this purpose are nitrogen, carbon dioxide, nitrous oxide, etc. Other suitable pharmaceutical carriers and their formulations are described in A. R. Alfonso Remington's Pharmaceutical Sciences 1985, 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001%w to 10.0%w of the compound of Formula I, preferably 0.00001%w to 1.0%w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 29.

CHEMISTRY:

Compounds of Formula I:

The compounds of Formula I can be prepared by the process depicted in Scheme 1.

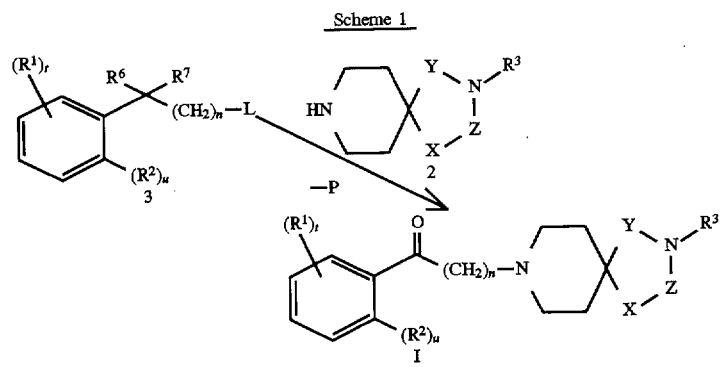

Scheme 1 in which L is a leaving group, $R^6$ and $R^7$ form oxo or a carbonyl protective group and each n, t, u, X, Y, Z, $R^1$, $R^2$ and $R^3$ are as defined in the Summary of the Invention with respect to Formula I.

Compounds of Formula I can be prepared by alkylating an appropriate heterocyclic spiro[4.5]decane (Formula 2), typically a salt thereof (e.g., hydrochloride, trifluoroacetate, hydrobromide, sulfate, etc.), with an appropriate 1-phenyl-1-($C_{3-7}$)alkanone or protected derivative thereof (Formula 3), and then deprotecting when necessary. The alkylation is carried out with 0.8 to 2 molar equivalents, typically 1 to 1.5 and preferably approximately 1.3 molar equivalents of the compound of Formula 2, in a suitable inert organic solvent (e.g., N,N-dimethylformamide (DMF), 1-methyl-2-pyrrolidone, N,N-dimethylacetamide, dimethylsulfoxide, sulfolane, 1,1,3,3-tetramethylurea, any appropriate mixture of suitable solvents, etc., preferably DMF) with a suitable base present, typically a nitrogen base (e.g., triethylamine, N,N-diisopropylethylamine, etc.) or a carbonate salt base (e.g., potassium carbonate, sodium carbonate, cesium carbonate, etc.) and preferably triethylamine, and optionally an iodide salt present (e.g., sodium iodide, lithium iodide, tetraalkylammonium iodides such as tetramethylammonium iodide and the like, etc., preferably sodium iodide) at 40° C.

proceeding as described above with respect to Scheme 1, but substituting approximately 2 molar equivalents, of the compound of Formula 3.

Deprotection when $R^6$ and $R^7$ comprise a carbonyl protective group can be effected by any means which removes the protective group and gives the desired product in reasonable yield. A detailed description of the techniques applicable to protective groups and their removal can be found in T. W. Greene, *Protective Groups in Organic Synthesis*, John Wiley & Sons, Inc. 1981. For example, a convenient method of deprotecting when the protective group is ethylenedioxy is carried out by acid-catalyzed exchange dioxolanation, by acid-catalyzed hydrolysis or oxidation. A preferred method of cleaving a ethylenedioxy protective group is by acid-catalyzed hydrolysis and is carried out with an appropriate acid (e.g., hydrochloric acid, oxalic acid, sulfuric acid, etc., preferably hydrochloric acid) in a suitable inert organic solvent, typically an aqueous alcohol (e.g., methanol, ethanol, 2-ethoxyethanol, any appropriate mixture of suitable alcohols, etc.) and preferably methanol or a dilute aqueous acid alone or in combination with a suitable solvent (e.g., THF, dioxane, any appropriate mixture of suitable solvents, etc.), typically at 20° to 85° C. and preferably at approximately 65° C. requiring 0.2 to 2 hours (for further details see Example 24, infra.).

Alternatively, compounds of Formula I can be prepared by the process depicted in Scheme 2.

Scheme 2

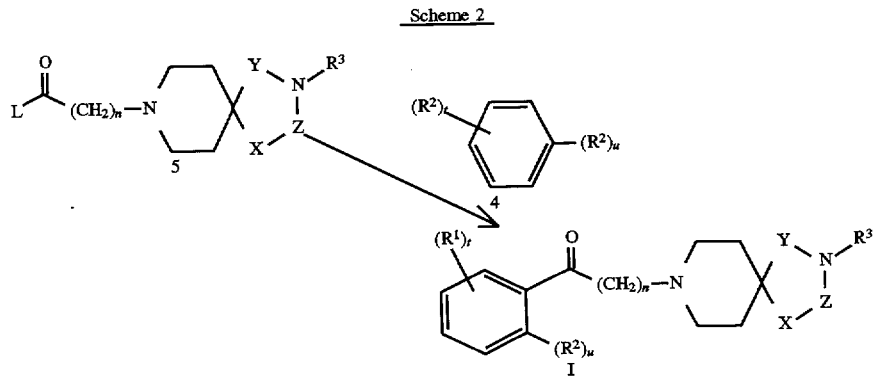

to 130° C., typically at 70° C. to 115° C. and preferably at approximately 110° C., requiring 4 to 24 hours (for further details see Example 23, infra.). Compounds of Formula I in which $R^3$ is a group of Formula (a) can be prepared by in which L is a leaving group and each n, t, u, X, Y, Z, $R^1$, $R^2$ and $R^3$ are as defined in the Summary of the Invention with respect to Formula I.

The compounds of Formula I can be prepared by acylating an appropriately substituted benzene derivative (Formula 4) with an activated ω-spiro[4.5]dec-8-yl-1-($C_{3-7}$) alkanone (Formula 5). The acylation is carried out in the presence of a Lewis acid (e.g., aluminum chloride ($AlCl_3$), boron trifluoride, hydrogen fluoride, phosphosporic acid, etc., preferably $AlCl_3$) in a suitable solvent (e.g., ethylene dichloride (EDC), methylene chloride, carbon disulfide, any appropriate mixture of suitable solvent, eta., preferably EDC) typically at 0° C. to 80° C. and preferably at approximately 25° C. requiring 12 to 48 hours.

Alternatively, compounds of Formula I in which X is NH, Y is C(O), Z is C(O) and $R^3$ is hydro can be prepared by the process depicted in the following Scheme 3.

bonate is carried out in a suitable solvent (e.g., methanol, ethanol-water, any appropriate mixture of suitable solvents, etc.) typically at 20° C. to 100° C. and preferably at approximately 65° C., requiring 2 to 8 hours. The deprotection is carried out by proceeding as described above with respect to Scheme 1.

Alternatively, compounds of Formula I in which X is O, Y is C(O), Z is C(O) and $R^3$ is hydro can be prepared by the process depicted in the following Scheme 4.

Scheme 3

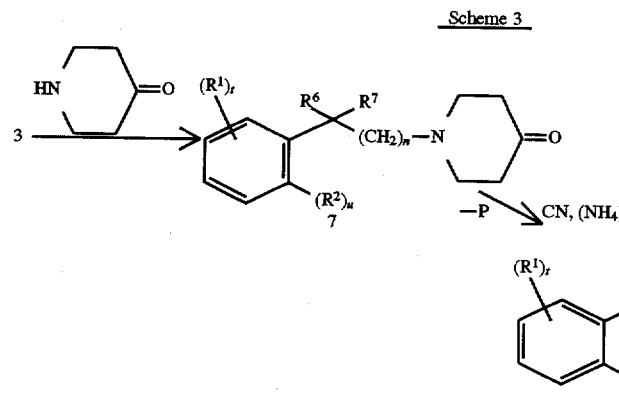

in which $R^6$ and $R^7$ form a carbonyl protective group and each n, t, u, $R^1$ and $R^2$ are as defined in the Summary of the Invention with respect Formula I.

Scheme 4

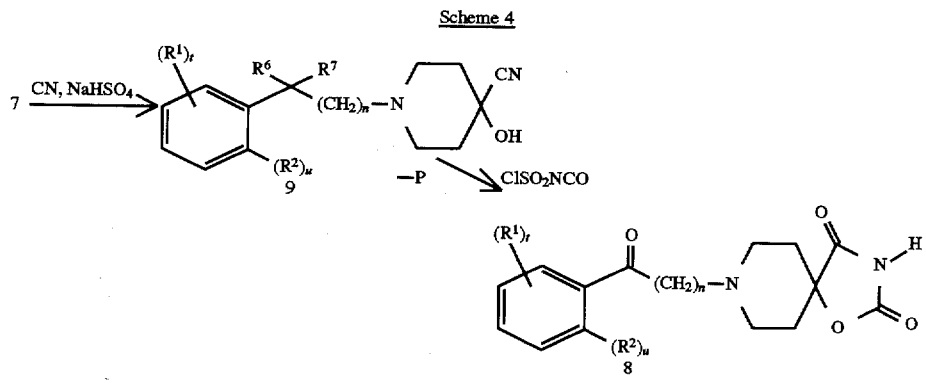

Compounds of Formula I in which X is NH, Y is C(O), Z is C(O) and $R^3$ is hydro (Formula 6) can be prepared by alkylating 4-piperidone with a compound of Formula 3 to give a corresponding 1-(ω-phenyl($C_{1-4}$)alkyl)-4-piperidone (Formula 7) and then reacting the compound of Formula 7 with an excess, preferably approximately 3 molar equivalents, of a cyanide salt (e.g., potassium cyanide, sodium cyanide, etc.) and an excess, preferably approximately 5 molar equivalents, of ammonium carbonate and deprotecting. The alkylation is carried out by proceeding as described above with respect to Scheme 1, but substituting the 4-piperidone for the compound of Formula 2. The reaction with the potassium cyanide and ammonium carin which $R^6$ and $R^7$ form oxo or a carbonyl protective group and each n, t, u, $R^1$ and $R^2$ are as defined in the Summary of the Invention with respect to Formula I.

Compounds of Formula I in which X is O, Y is C(O), Z is C(O) and $R^3$ is hydro (Formula 8) can be prepared by reacting a compound of Formula 7 with a slight excess, preferably approximately 1.4 molar equivalents, of a cyanide salt (e.g., potassium cyanide, sodium cyanide, etc.) and a slight excess, preferably approximately 1.1 molar equivalents, of sodium bisulfate to give a corresponding 4-hydroxy-1-(ω-phenyl($C_{3-7}$)alkyl)-4-piperidinecarbonitrile (Formula 9) and then reacting the compound of Formula 9 with chlorosulfonyl isocyanate and deprotecting when necessary. The reaction with the cyanide salt and sodium bisulfate is carried out in a suitable solvent (e.g., water, alcohol-water, acetonitrile, any appropriate mixture of suitable solvents, etc., preferably water) typically at 10° C. to 100° C. and preferably at approximately 25° C. requiring 0.2 to 8 hours. The reaction with the isocyanate is carried out in a suitable solvent (e.g., toluene, dioxane, any appropriate mixture of suitable solvents, etc., preferably toluene) typically at reflux. The deprotection is carried out by proceeding as described above with respect to Scheme 1.

Alternatively, compounds of Formula I in which X is O, Y is CH$_2$ and Z is C(O) or C(S) can be prepared by the process depicted in the following Scheme 5.

thiocarbonyldiimidazole, respectively, and deprotecting when necessary. The reaction with the trimethylsulfoxonium iodide is carried out in the presence of a strong base (e.g., sodium hydride, potassium hydride, tert-butyllithium, sodium tert-butoxide, etc., preferably sodium hydride), typically under an inert atmosphere (e.g., argon, nitrogen, etc.), in a suitable solvent (e.g., DMSO, sulfolane, etc., preferably DMSO), typically at 20° C. to 60° C. and preferably at approximately 50° C. and requires 0.5 to 2 hours.

The amination is carried out in a suitable solvent (e.g., 1-methylpyrrolidone, dioxane, THF, etc., preferably THF), typically at 50° C. to 120° C. and preferably at approximately 100° C. and requires 16 to 24 hours. The reaction

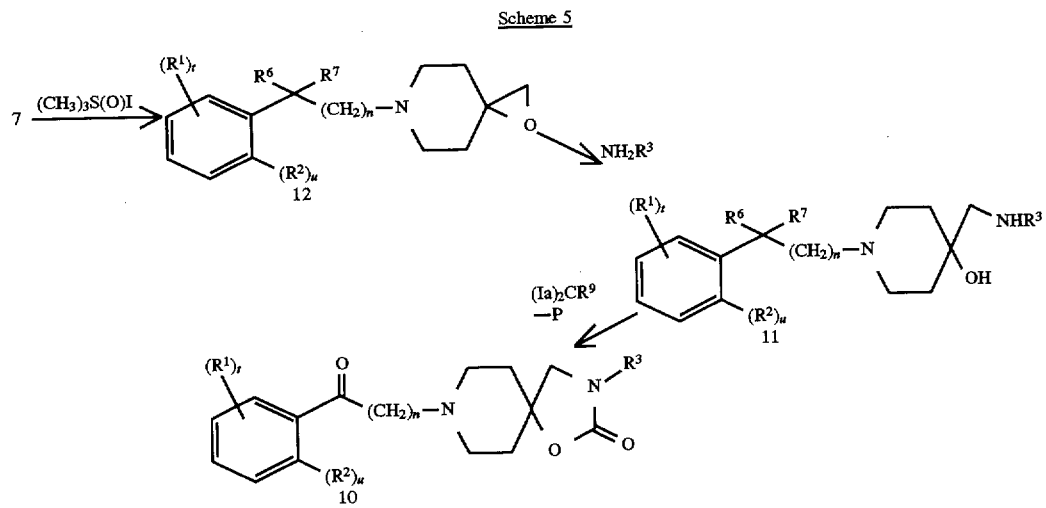

Scheme 5 in which R$^6$ and R$^7$ form oxo or a carbonyl protective group, R$^9$ is O or S and each n, t, u, R$^1$, R$^2$ and R$^3$ are as defined in the Summary of the Invention with respect to Formula I.

Compounds of Formula I in which X is O, Y is CH$_2$ and Z is C(O) or C(S) (Formula 10) can be prepared by reacting a compound of Formula 7 with trimethylsulfoxonium iodide to give a corresponding ω-(6-aza-1-oxaspiro[2.3]oct-6-yl)-1-phenyl-1-(C$_{3-7}$)alkanone (Formula 12), aminating the compound of Formula 12 with an amine of the formula NH$_2$R$^3$ to give a corresponding ω-(4-aminomethyl-4-hydroxypiperidin-1-yl)-1-phenyl-1-(C$_{3-7}$)alkanone (Formula 11) and then reacting the compound of Formula 11 with 1,1'-carbonyldiimidazole or 1,1'- with the diimidazole is carried out in a suitable solvent (e.g., DMF, THF, dioxane, any appropriate mixture of suitable solvents, etc., preferably THF) typically at 40° to 120° C. and preferably at 80° C. to 100° C. requiring 3 to 12 hours. The deprotection is carried out by proceeding as described above with respect to Scheme 1.

Alternatively, compounds of Formula I in which X is NH, Y is C(S) and Z is C(O) or C(S) can be prepared by the process depicted in the following Scheme 6.

Scheme 6

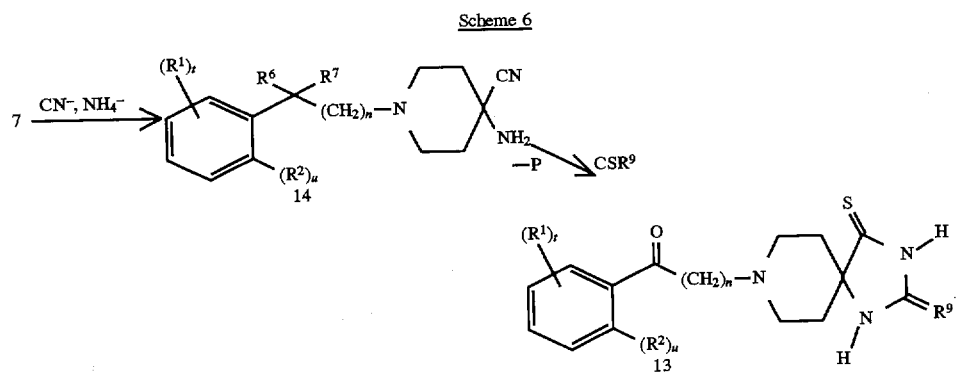

in which $R^6$ and $R^7$ form a carbonyl protective group, $R^9$ is O or S and each n, t, u, $R^1$, $R^2$ and $R^3$ are as defined in the Summary of the Invention with respect to Formula I.

Compounds of Formula I in which X is NH, Y is C(S) and Z is C(O) or C(S) (Formula 13) can be prepared by reacting a compound of Formula 7 with an excess, preferably approximately 2 molar equivalents of a cyanide salt (e.g., potassium cyanide, sodium cyanide, etc.) and an excess of an ammonium salt (e.g., ammonium hydroxide, ammonium chloride, any appropriate mixture of ammonium salts, etc.), preferably approximately 2.5 molar equivalents each of ammonium chloride and ammonium hydroxide, to give a corresponding 4-amino-1-(ω-phenyl($C_{3-7}$)alkyl)piperidine-4-carbonitrile (Formula 14) and then reacting the compound of Formula 14 with carbon oxysulfide or carbon disulfide, respectively, and deprotecting when necessary. The reaction with the cyanide salt and ammonium salt is carried out in a suitable solvent, typically an aqueous alcohol (e.g., methanol, ethanol, 2-ethoxyethanol, any appropriate mixture of suitable alcohols, etc.) and preferably methanol, at 0° C. to 70° C. typically at 25° C. to 50° C. and preferably at approximately 50° C. requiring 2 to 16 hours (for further details see Example 20, infra.). The reaction with the carbon oxysulfide or carbon disulfide can be carried out in the same solvent system and essentially under the same reaction conditions as those describe above. Alternatively, Scheme 1 can be carried out with the carbon oxysulfide or carbon disulfide present from the beginning and heating at 40° C. to 50° C. for 4 to 24 hours. The deprotection is carried out by proceeding as described above with respect to Scheme 1.

Alternatively, compounds of Formula I in which X is NH, Y is C(O) and Z is C(O) or C(S) can be prepared by the process depicted in the following Scheme 7.

see Example 21, infra-) or a base (e.g., potassium hydroxide or the like) at 20° C. to 80° C. If $R^6$ and $R^7$ form an acid-labile carbonyl protective group, the protective group generally will be removed with acid hydrolyzation. The reaction with the diimidazole is carried out in a suitable solvent (e.g., DMF, THF, dioxane, any appropriate mixture of suitable solvents, etc., preferably DMF) typically at 15° C. to 75° C. and preferably at approximately 55° C. requiring 2 to 12 hours (for further details see Example 22, infra.). The deprotection is carried out by proceeding as described above with respect to Scheme 1.

Additional Processes for Preparing Compounds of Formula I:

Compounds of Formula I in which $R^1$ is amino can be prepared by reducing a compound of Formula I in which $R^1$ is nitro. The reduction can be carried out with a suitable chemical reducing agent or by catalytic hydrogenation. For example, the reduction is conveniently carried out by hydrogenating in the presence of a suitable catalyst (e.g., 5 or 10% Pd/C, palladium hydroxide, platinum oxide, palladium, palladium oxide, nickel, palladium acetate, etc., preferably 10% Pd/C) in a suitable solvent (e.g., THF, DMF, methanol, ethyl acetate, ethanol, acetic acid, any appropriate mixture of suitable solvents, etc.) at 20° to 40° C., typically at 20° C. to 30° C. and preferably at approximately 25° C., and 15 to 70 psi, typically at 15 to 30 psi and preferably at approximately 15 psi, and requires 0.5 to 24 hours (for further details see Example 25, infra.).

Compounds of Formula I in which $R^1$ is —NHC(S)NHR$^5$, in which $R^5$ is as defined in the Summary of the Invention with respect to Formula I, can be prepared by reacting a compound of Formula I in which $R^1$ is amino with an appropriate isothiocyanate of the formula $R^5NC(S)$. The

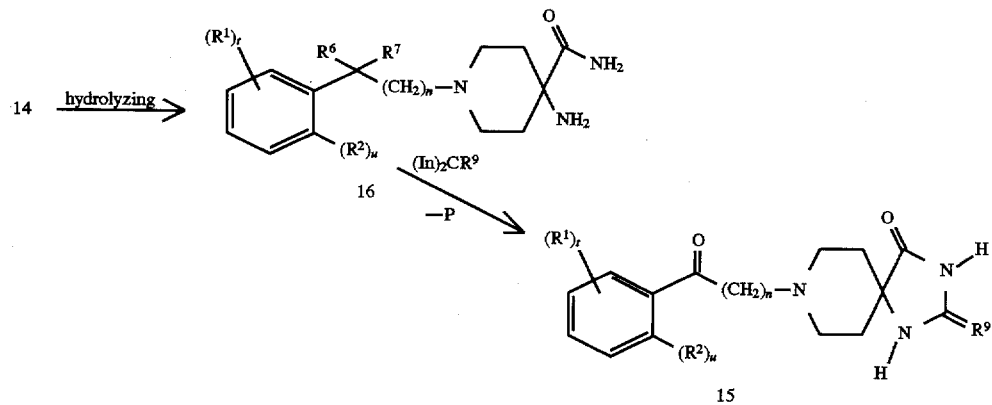

Scheme 7 in which $R^6$ and $R^7$ form oxo or a carbonyl protective group, $R^9$ is O or S and each n, t, u, $R^1$, and $R^2$ are as defined in the Summary of the Invention with respect to Formula I.

Compounds of Formula I in which X is NH, Y is C(O) and Z is C(O) or C(S) (Formula 15) can be prepared by hydrolyzing a compound of Formula 14 to give a corresponding 4-amino-1-(ω-phenyl($C_{1-7}$)alkyl)-4-piperidinecarboxamide (Formula 16) and then reacting the compound of Formula 16 with 1,1'-carbonyldiimidazole or 1,1'-thiocarbonyldiimidazole, respectively, and deprotecting when necessary. The hydrolysis can be effected with an aqueous acid (e.g., sulfuric acid, hydrochloric acid, etc.) typically at 20° to 120° C. and preferably at approximately 100° C. and requires 5 minutes to 2 hours (for further details reaction is carried out in a suitable solvent (e.g., toluene, N-methyl-2-pyrrolidinone, DMF, 1,1,3,3-tetramethylurea, THF, dioxane, any appropriate mixture of suitable solvents, etc., preferably toluene or N-methyl-2-pyrrolidinone) at −10° C. to 70° C., typically at 15° C. to 40° C. and preferably at approximately 25° C. requiring 10 minutes to 8 hours (for further details see Example 26, infra.). Proceeding similarly, but substituting for the isothiocyanate an appropriate isocyanate of the formula $R^5NC(O)$ compounds of Formula I in which $R^1$ is —NHC(O)NHR$^5$ can be prepared.

Compounds of Formula I in which $R^1$ is —NHSO$_2R^5$, in which $R^5$ is as defined in the Summary of the Invention with respect to Formula I, can be prepared by reacting a compound of Formula I in which $R^1$ is amino with an appropriate sulfonyl halide (e.g., 4-trifluorobenzenesulfonyl chloride, 1-pyrrolidinesulfonyl chloride, 3-(5-trifluoromethyl-1-methylpyrazol-3-yl)-2-thiophenesulfonyl chloride, etc.). The reaction is carried out in the presence of a suitable base (e.g., triethylamine, diisopropylethylamine, etc.) and in a suitable solvent (e.g., THF, 1-methyl-2-pyrrolidinone, DMF, dichloroethane, any appropriate mixture of suitable solvents, etc., preferably THF) at 0° to 60° C. preferably at approximately 25° C. requiring 0.5 to 24 hours (for further details see Example 27, infra.).

Compounds of Formula I in which $R^3$ is $(C_{1-6})$alkyl (optionally substituted with a group selected from —C(O)OH, —C(O)O($C_{1-4}$)alkyl, —NHSO$_2R^5$ and —NHC(O)$R^5$, in which $R^5$ is as defined in the Summary of the Invention with respect to Formula I), hydroxyalkyl, esterified hydroxyalkyl, —CH$_2$O($C_{1-4}$)alkyl, —CH$_2$OC(O) ($C_{1-4}$) alkyl, phenyl ($C_{1-4}$)alkyl (optionally substituted with one or two radicals independently selected from amino, cyano, halo, hydroxy, nitro, trifluoromethyl, trifluoromethoxy, acetamido, methanesulfonamido, ($C_{1-4}$)alkyl, or ($C_{1-4}$) alkyloxy), or a group of Formula (a) can be prepared by reacting a compound of Formula I in which $R^3$ is hydro with a suitable alkylating agent (e.g., a compound of Formula 3). The reaction is carried out in a suitable solvent (e.g., DMF, any appropriate mixture of suitable solvents, etc.) typically at −10° C. to 40° C. and preferably at approximately 15° C., requiring 0.5 to 8 hours.

Compounds of Formula I in which $R^3$ is esterified hydroxyalkyl can be prepared by esterification of a compound of Formula I in which $R^3$ is hydroxyalkyl, such as by reaction with an acyl halide of the appropriate alkanoic or amino acid.

The N-oxides of the compounds of Formula I can be prepared by treating an unoxidized form of the compound of Formula I with an oxidizing agent (e.g., trifluoroperacetic acid, permaleic acid, perbenzoic acid, peracetic acid, metachloroperoxybenzoic acid, etc.) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0° C. to 80° C.

Compounds of Formula I may be prepared as pharmaceutically acceptable acid addition salts by reacting the free base forms of a compound of Formula I with a pharmaceutically acceptable inorganic or organic acid. Alternatively, the pharmaceutically-acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

In summary, an aspect of this invention is a process for preparing a compound of Formula I:

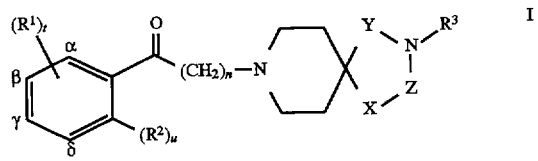

in which:

n is 2, 3, 4, 5 or 6;

t is 1, 2, 3 or 4 and u is 0 or 1 (provided that t is not 1 when u is 0);

X is O or N($R^4$);

Y and Z are independently C(O), C(S) or CH$_2$ (provided that Y and Z are not both CH$_2$); each $R^1$ is independently amino, aryloxy, aryl($C_{1-4}$)alkyloxy, arylsulfonyl, arylthio, carbamoyl, cyano, halo, nitro, thiocarbamoyl, thioureido, ureido, a group selected from ($C_{1-4}$)alkyl, ($C_{1-4}$)alkyloxy and ($C_{1-4}$)alkylthio (optionally further substituted with one to three halo atoms), a group selected from —NHSO$_2R^5$, —NHC(O)$R^5$, —NHC(O)NHR$^5$, —NHC(S)NHR$^5$ and —SO$_2$NHR$^5$ {which $R^5$ is ($C_{1-4}$)alkyl (optionally further substituted with one to three halo atoms) or a group selected from aryl, aryl ($C_{1-4}$)alkyl, heteroaryl and heteroaryl ($C_{1-4}$)alkyl (optionally further substituted with one to two radicals independently selected from amino, carbamoyl, cyano, halo, nitro, a group selected from ($C_{1-4}$)alkanoyl, ($C_{1-4}$)alkylsulfonylamino, ($C_{1-4}$) alkanoylamino, ($C_{1-4}$)alkyl and ($C_{1-4}$)alkyloxy, optionally further substituted with one to three halo atoms, and a group selected from aryl, arylsulfonyl, heteroaryl and heteroarylsulfonyl, optionally further substituted with one to two radicals independently selected from amino, cyano, halo, nitro and a group selected from ($C_{1-4}$)alkyl and ($C_{1-4}$)alkyloxy, optionally further substituted with one to three halo atoms)} or with an adjacent $R^1$ radical form ethylenedioxy, methylenedioxy or butadienylene (which butadienylene is optionally further substituted with one to two radicals selected from halo and ($C_{1-4}$)alkyloxy);

$R^2$ is hydroxy, halo, ($C_{1-4}$)alkyloxy or aryl ($C_{1-4}$) alkyloxy;

$R^3$ is hydro, ($C_{1-6}$)alkyl (optionally substituted with a group selected from —C(O)OH, —C(O)O($C_{1-4}$)alkyl, —NHSO$_2R^5$ and —NHC(O)$R^5$, in which $R^5$ is as defined above), hydroxyalkyl, esterified hydroxyalkyl, —CH$_2$O($C_{1-4}$)alkyl, —CH$_2$OC(O) ($C_{1-4}$)alkyl, phenyl ($C_{1-4}$)alkyl (optionally substituted with one or two radicals independently selected from amino, cyano, halo, hydroxy, nitro, trifluoromethyl, trifluoromethoxy, acetamido, methanesulfonamido, ($C_{1-4}$)alkyl, or ($C_{1-4}$) alkyloxy), or a group of Formula (a):

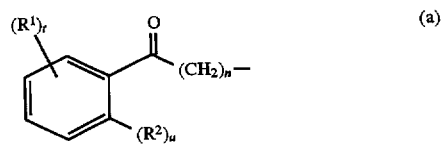

in which each n, t and $R^1$ are as defined above with respect to Formula I; and $R^4$ is hydro, $(C_{1-4})$alkyl, or aryl, or $R^4$ and $R^3$ are the same and are —$CH_2O(C_{1-4})$alkyl or —$CH_2OC(O)$ $(C_{1-4})$ alkyl;

and the pharmaceutically acceptable salts and N-oxides thereof, which process comprises:

(a) alkylating a compound of Formula 2:

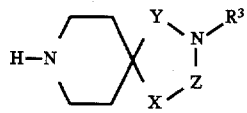
2 with a compound of Formula 3:

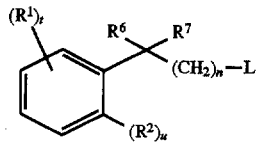
3 in which L is a leaving group and $R^6$ and $R^7$ form oxo or a carbonyl protective group, and deprotecting when necessary to give a compound of Formula I in which each n, t, u, X, Y, Z and $R^1$, $R^2$ and $R^3$ are as defined above with respect to Formula I; or (b) acylating a compound of Formula 4:

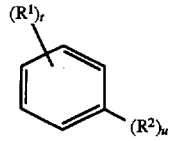
4 with a compound of Formula 5:

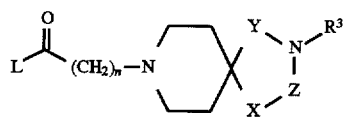
5 in which L is a leaving group, to give a compound of Formula I in which each n, t, u, X, Y, Z, $R^1$, $R^2$ and $R^3$ are as defined above with respect to Formula I; or (c) (1) alkylating 4-piperidone with a compound of Formula 3 to give a compound of Formula 7:

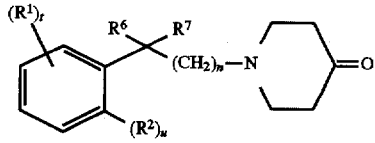
7 in which $R^6$ and $R^7$ form oxo or a carbonyl protective group, (2) reacting the compound of Formula 7 with a cyanide salt and ammonium carbonate and deprotecting when necessary to give a compound of Formula I in which X is NH, Y is C(O), Z is C(O), $R^3$ is hydro, and each n, t, u, $R^1$, and $R^2$ are as defined above with respect to Formula I; or (d) (1) reacting a compound of Formula 7 with a cyanide salt and sodium bisulfate to give a compound of Formula 9:

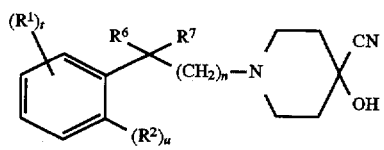
9 in which $R^6$ and $R^7$ form oxo or a carbonyl protective group, and (2) reacting the compound of Formula 9 with chlorosulfonyl isocyanate and deprotecting when necessary to give a compound of Formula I in which X is O, Y is C(O), Z is C(O), $R^3$ is hydro and each n, t, u, $R^1$ and $R^2$ are as defined above; or (e) (1) reacting a compound of Formula 7 with trimethylsulfoxonium iodide to give a compound of Formula 12:

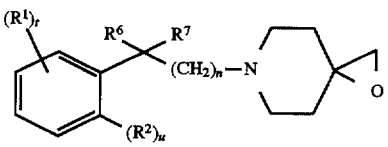
12 in which $R^6$ and $R^7$ form oxo or a carbonyl protective group, (2) aminating the compound of Formula 12 with an amine of the formula to give a compound of Formula 11:

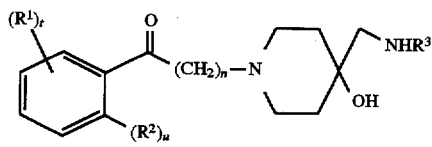
11 and (3) reacting the compound of Formula 11 with 1,1'-carbonyldiimidazole or 1,1'-thiocarbonyldiimidazole and deprotecting when necessary to give a compound of Formula I in which X is O, Y is $CH_2$ and Z is C(O) or C(S), respectively; or (f) (1) reacting a compound of Formula 7 with a cyanide salt and an ammonium salt to give a compound of Formula 14:

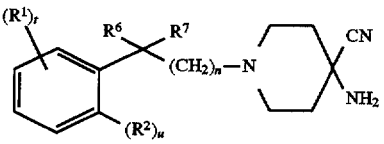
14 in which $R^6$ and $R^7$ form oxo or a carbonyl protective group and (2) reacting the compound of Formula 14 with carbon oxysulfide or carbon disulfide and deprotecting when necessary to give a compound of Formula I in which X is NH, Y is C(S) and Z is C(O) or C(S), respectively; or (g) (1) hydrolyzing a compound of Formula 14 to give a compound of Formula 16:

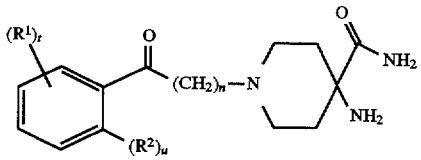
16 and (2) reacting the compound of Formula 16 with 1,1'-carbonyldiimidazole or 1,1'-thiocarbonyldiimidazole to give a compound of Formula I in which X is NH, Y is C(O) and Z is C(O) or C(S), respectively;

(h) optionally further reducing a compound of Formula I in which $R^1$ is nitro to give a compound of Formula I in which $R^1$ is amino;

(i) optionally further reacting a compound of Formula I in which $R^1$ is amino with an isothiocyanate of the formula $R^5NC(S)$, in which $R^5$ is as defined above with respect to Formula I, to give a corresponding compound of Formula I in which $R^1$ is —NHC(S)NHR$^5$;

(j) optionally further reacting a compound of Formula I in which $R^1$ is amino with an isocyanate of the formula $R^5NC(O)$, in which $R^5$ is as defined above with respect to Formula I, to give a corresponding compound of Formula I in which $R^1$ is —NHC(O)NHR$^5$;

(k) optionally further reacting a compound of Formula I in which $R^1$ is amino with an appropriate sulfonyl halide to give a compound of Formula I in which $R^1$ is —NHSO$_2$R$^5$, wherein $R^5$ is as defined above with respect to Formula I;

(l) optionally further alkylating a compound of Formula I in which $R^3$ is hydro with a suitable alkylating agent to give a compound of Formula I in which $R^3$ is hydro, $(C_{1-6})$alkyl (optionally substituted with a group selected from —C(O)OH, —C(O)O($C_{1-4}$)alkyl, —NHSO$_2$R$^5$ and —NHC(O)R$^5$, in which $R^5$ is as defined above), hydroxyalkyl, phenyl ($C_{1-4}$)alkyl (optionally substituted with one or two radicals independently selected from amino, cyano, halo, hydroxy, nitro, trifluoromethyl, trifluoromethoxy, acetamido, methanesulfonamido, ($C_{1-4}$)alkyl, or ($C_{1-4}$)alkyloxy), or a group of Formula (a);

(m) de-alkylating a compound of Formula I in which $R^3$ is ($C_{1-6}$)alkyl to give a compound of Formula I in which $R^3$ is hydro;

(n) optionally further oxidizing a compound of Formula I to give an N-oxide derivative thereof;

(o) optionally further reducing an N-oxide derivative of a compound of Formula I to unoxidized form;

(p) optionally further converting a compound of Formula I into a pharmaceutically acceptable salt; and (q) optionally further converting a salt form of a compound of Formula I to non-salt form.

In any of the above processes, a reference to Formula I refers to such Formula wherein each n, t, u, X, Y, Z, $R^1$, $R^2$ and $R^3$ are as defined in their broadest definitions set forth in the Summary of the Invention, with the processes applying particularly well to the presently preferred embodiments. Compounds of Formula 2:

Compounds of Formula 2 in which X is NH, Y is C(O), Z is C(O) and $R^3$ is hydro (i.e., 1,3,8-triazaspiro[4.5]decane-2,4-diones) can be prepared by reacting a protected 4-piperidone (e.g., tert-butyl 4-oxopiperidine-1-carboxylate, 1-benzyl-4-piperidone, etc.) with cyanide salt and ammonium carbonate and then deprotecting. The reaction for preparing the protected 1,3,8-triazaspiro[4.5]decane-2,4-dione is carried out by proceeding as described above with respect to Scheme 3, but substituting the 4-piperidone for the compound of Formula 7. A convenient method of deprotecting when the protective group is tert-butoxycarbonyl is carried out with acid (e.g., hydrochloric acid, trifluoroacetic acid, etc.) with or without a suitable co-solvent (e.g., methanol, ethanol, 2-ethoxyethanol, any appropriate mixture of suitable alcohols, etc., preferably ethanol) at 0° C. to 100° C. typically at 20° C. to 80° C. and preferably at reflux, requiring 0.1 to 2 hours. Further details of the reaction steps set forth in this paragraph are provided in Example 16, infra.

Compounds of Formula 2 in which X is O, Y is C(O), Z is C(O) and $R^3$ is hydro (i.e., 3,8-diaza-1-oxaspiro[4.5]decane-2,4-diones) can be prepared by reacting a protected 4-piperidone with a cyanide salt and sodium bisulfate to give the corresponding 4-hydroxypiperidine-4-carbonitrile, reacting the nitrile with chlorosulfonyl isocyanate and then deprotecting. The process steps for preparing the protected 3,8-diaza-1-oxaspiro[4.5]decane-2,4-diones are carried out by proceeding as described above with respect to Scheme 4, but substituting the 4-piperidone for the compound of Formula 7 (for further details see Example 17, infra.).

Compounds of Formula 2 in which X is O, Y is CH$_2$ and Z is C(O) or C(S) (i.e., 3,8-diaza-1-oxaspiro[4.5]decane-2-ones and -2-thiones) can be prepared by reacting a protected 4-piperidone with trimethylsulfoxonium iodide to give the corresponding 6-aza-1-oxaspiro[2.3]octane, aminating the spirooctane with an amine of the formula NH$_2$R$^3$ to give the corresponding 4-aminomethyl-4-hydroxypiperidine, reacting the piperidine with 1,1'-carbonyldiimidazole or 1,1'-thiocarbonyldiimidazole, respectively, and deprotecting. The process steps for preparing the protected 3,8-diaza-1-oxaspiro[4.5]decane-2-ones and -2-thiones are carried out by proceeding as described above with respect to Scheme 5, but substituting the 4-piperidone for the compound of Formula 7 (for further details see Example 18, infra.).

Compounds of Formula 2 in which X is NH, Y is C(S) and Z is C(O) or C(S) and $R^3$ is hydro (i.e., 4-thioxo-1,3,8-triazaspiro[4.5]decane-2-ones and 1,3,8-triazaspiro[4.5]decane-2,4-dithiones) can be prepared by reacting a protected 4-piperidone with a cyanide salt and an ammonium salt to give the corresponding 4-aminopiperidine-4-carbonitrile, reacting the nitrile with carbon oxysulfide or carbon disulfide, respectively, and deprotecting. The process steps for preparing the protected 3,8-diaza-1-oxaspiro[4.5]decane-2-ones and 1,3,8-triazaspiro[4.5]decane-2,4-dithiones are carried out by proceeding as described above with respect to Scheme 6, but substituting the 4-piperidone for the compound of Formula 7.

Compounds of Formula 2 in which X is NH, Y is C(O) and Z is C(O) or C(S) and $R^3$ is hydro (i.e., 1,3,8-triazaspiro[4.5]decane-2,4-diones and 2-thioxo-1,3,8-triazaspiro[4.5]decane-4-ones) can be prepared by hydrolyzing a corresponding 4-aminopiperidine-4-carbonitrile, prepared as describe above in the preceding paragraph, to give the corresponding 4-aminopiperidine-4-carboxamide, reacting the carboxamide with 1,1'-carbonyldiimidazole or 1,1'-thiocarbonyldiimidazole, respectively, and then deprotecting. The process steps for preparing the protected 1,3,8-triazaspiro[4.5]decanones are carried out by proceeding as described above with respect to Scheme 7, but substituting the 4-aminopiperidine-4-carbonitrile for the compound of Formula 14. A convenient method of deprotecting when the protective group is benzyl is carried out by hydrogenating in the presence of a suitable catalyst (e.g., 10% Pd/C, palladium hydroxide, palladium, palladium oxide, nickel, palladium acetate, etc., preferably 10% Pd/C) optionally in the presence of acid and in a suitable solvent, typically an alcohol (e.g., methanol, ethanol, 2-ethoxyethanol, any appropriate mixture of suitable alcohols, etc.) or an alcohol/water mixture and preferably ethanol, typically at 0° C. to 100° C. and preferably at approximately 25° C. and typically at 15 to 60 psi and preferably at approximately 50 psi.

Compounds of Formula 2 in which $R^3$ is hydro, optionally substituted ($C_{1-6}$)alkyl, hydroxyalkyl, esterified hydroxyalkyl, or optionally substituted phenyl $(C_{1-4})$alkyl can be prepared by alkylating a compound of Formula 2 in which $R^3$ is hydro. The reaction is carried out with an appropriate alkylating agent (e.g., dimethylsulfate, N-(3-chloropropyl)-4-methoxybenzenesulfonamide, etc.) in a suitable solvent (e.g., DMF, water, 1-methyl-2-pyrrolidinone, any appropriate mixture of suitable solvents, etc., preferably DMF) at −20° to 40° C. typically at 0° C. to 40° C. and preferably at approximately 25° C. (for further details see Example 19, infra.).

Compounds of Formula 2 in which $R^3$ is $-CH_2O(C_{1-4})$alkyl or $-CH_2OC(O)$ $(C_{1-4})$alkyl, and compounds of Formula 2 in which X is $N(R^4)$ and $R^4$ and $R^3$ are the same and are $-CH_2O(C_{1-4})$alkyl or $-CH_2OC(O)$ $(C_{1-4})$alkyl can be prepared by modifications of the methods described in Samour et al. (1971), *J. Med. Chem.*, 14, 187–189; Vida et al. (1971), *J. Med. Chem.*, 14, 190–193; Vida et al. (1975), *J. Med. Chem.*, 18, 383–385, for the synthesis of substituted hydantoins.

Compounds of Formula 3:

Compounds of Formula 3 can be prepared by reacting an appropriately substituted benzoic acid chloride with N,O-dimethylhydroxylamine hydrochloride to give a compound of Formula 17:

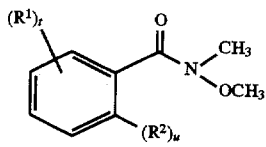

17 in which each t, u, $R^1$ and $R^2$ are as defined in the Summary of the Invention with respect to Formula I (provided that $R^1$ cannot be amino, nitro, thiocarbamoyl, thioureido, ureido, $-NHSO_2R^5$, $-NHC(O)R^5$, $-NHC(O)NHR^5$, $-NHC(S)NHR^5$ and $-SO_2NHR^5$) and reacting the compound of Formula 17 with a 1-metalated ω-halo($C_{2-6}$)alkane, typically a lithium ω-halo-1-($C_{2-6}$)alkanide and preferably a lithium ω-chloro-1-($C_{2-5}$)alkanide. Suitable benzoic acid chlorides are prepared by reacting a correspondingly substituted benzoic acid with an appropriate halogenating agent (e.g., thionyl chloride, oxalyl chloride, phosphorus pentachloride, etc.) and in a suitable solvent (e.g., methylene chloride, dichloroethane, any appropriate mixture of suitable solvents, etc., preferably methylene chloride) at 10° C. to 40° C. typically at 15° C. to 30° C. and preferably at approximately 25° C. and requires 2 to 18 hours. Suitably substituted benzoic acids are commercially available or can be prepared by methods known in the art (for further details see Examples 1, 2 and 3, infra.).

The reaction with the N,O-dimethylhydroxylamine hydrochloride is carried out in a suitable solvent (e.g., methylene chloride, THF, ethyl acetate, any appropriate mixture of suitable solvents, etc., preferably a mixture of THF and methylene chloride) at −10° C. to 80° C. typically at 0° C. to 50° C. and preferably at 25° C. and requires 0.2 to 6 hours. The 1-metalated ω-haloalkane is prepared by cooling a solution of an appropriate dihaloalkane, typically a ω-chloro-1-iodo($C_{2-5}$)alkane, in a suitable inert organic solvent, preferably an ether (e.g., THF, diethyl ether, any appropriate mixture of suitable solvents, etc., preferably a mixture of diethyl ether and pentane), typically to between −90° C. and −35° C. and preferably to approximately −65° C. adding an organometallic base, typically an alkylmetallic base and preferably an alkyl alkali metal base (e.g., t-butyllithium, n-butyllithium, s-butyllithium, n-butylsodium, n-butylpotassium, lithium diisopropylamide (LDA), etc., preferably t-butyllithium), at a rate such that the reaction temperature remains below −45° C., preferably below −55° C. and then allowing the reaction to proceed at approximately −60° C. for 10 minutes to 5 hours. The compound of Formula 17 is then added as a solution to the cooled mixture containing the 1-metalated ω-haloalkane at a rate such that the reaction temperature remains below −40° C. and then the reaction mixture is allowed to gradually warm to between −20° C. to 20° C. preferably to approximately 15° C. over 1 to 6 hours. Further details of the reaction steps set forth in this and the preceding paragraph are provided in Example 7, infra.

Compounds of Formula 3 in which $R^1$ is halo can be prepared by first halogenating the corresponding compound of Formula 17 in which $R^1$ is hydro. The halogenation is carried out with a suitable halogenating agent (e.g., N-chlorosuccinimide, chlorine, 1,3-dichloro-5,5-dimethylhydantoin, etc.) in a suitable solvent (e.g., acetonitrile, acetic acid, DMF, any appropriate mixture of suitable solvents, etc., preferably acetonitrile) preferably at approximately 50° C. (for further details see Example 5, infra.).

Alternatively, compounds of Formula 3 can be prepared by acylating an appropriately substituted benzene derivative of Formula 4 with an appropriate activated 1-($C_{3-7}$)alkanone (i.e., of the formula $LC(O)(CH_2)_nL$ in which L is a leaving group, preferably wherein n is 6). The acylation is carried out by proceeding as described above with respect to Scheme 2, but substituting the activated 1-($C_{3-7}$)alkanone for the compound of Formula 5 (for further details see Example 8, infra.).

Compounds of Formula 3 in which t is 2, u is 0 and two adjacent $R^1$ radicals form α,β-ethylenedioxy can be conveniently prepared by acylating 6,7-dichloro-1,4-benzodioxan with an appropriate activated 1-($C_{3-7}$)alkanone and then removing the chloro groups. Removal of the chloro groups can be effected by stirring under a hydrogen atmosphere with a suitable base (e.g., sodium hydroxide, lithium hydroxide, sodium acetate, etc.) and an appropriate catalyst (e.g., 10% Pd/C, nickel, etc, preferably 10% Pd/C) in a suitable solvent, typically an alcohol (e.g., methanol, ethanol, 2-ethoxyethanol, any appropriate mixture of suitable alcohols, etc.) and preferably methanol, at 0° C. to 60° C. typically at 15° C. to 40° C. and preferably at approximately 25° C., requiring 2 to 48 hours (for further details see Example 9, infra.).

Compounds of Formula 3 in which $R^6$ and $R^7$ form a carbonyl protective group can be prepared by reacting a compound of Formula 3 in which $R^6$ and $R^7$ form oxo with a suitable protecting agent (e.g., ethylene glycol). For example, a compound of Formula 3 in which $R^6$ and $R^7$ form ethylenedioxy can be prepared by reacting the unprotected compound of Formula 3 with ethylene glycol in a suitable inert organic solvent (e.g., toluene, benzene, any appropriate mixture of suitable solvents, etc., preferably toluene) and preferably at reflux (for further details see Example 10, infra.).

Compounds of Formula 3 in which $R^2$ is $(C_{1-4})$alkyloxy or aryl$(C_{1-4})$alkyloxy can be prepared by reacting a compound of Formula 3 in which $R^2$ is hydroxy with a suitable alkylating agent (e.g., iodomethane, dimethysulfate, iodoethane, benzylchloride, 2-iodopropane, etc.). Typically, $R^6$ and $R^7$ comprise a carbonyl protective group, preferably ethylenedioxy, when n is 2 or 3. The alkylation is carried out in the presence of a suitable base (e.g., sodium hydride, potassium carbonate, diisopropylethylamine, etc., preferably sodium hydride) in a suitable inert organic solvent (e.g., DMF, 2-butanone, 1-methyl-2-pyrrolidinone, any appropriate mixture of suitable solvents, etc., preferably DMF) at −10° C. to 60° C. typically at 0° C. to 40° C. and preferably at approximately 25° C. and requires 0.5 to 8 hours (for further details see Example 11, infra.). The protective group is optionally removed by proceeding as described above with respect to Scheme 1.

Compounds of Formula 3 in which $R^1$ is nitro can be prepared by nitrating a compound of Formula 3 in which $R^1$ is hydro with a suitable nitrating agent (e.g., acetyl nitrate, nitric acid, sodium nitrate, etc.) in a suitable solvent (e.g., acetic anhydride, acetic acid, any appropriate mixture of suitable solvents, etc., preferably acetic anhydride). For example, the nitration can be conveniently carried out with acetyl nitrate, typically formed in situ by reaction of copper (II) nitrate with acetic anhydride, at 0° C. to 30° C. typically at to 20° C. and preferably at approximately 15° C., and requires 2 to 8 hours (for further details see Example 12, infra.).

Compounds of Formula 3 in which $R^1$ is amino can be prepared by reducing a compound of Formula 3 in which $R^1$ is nitro. The reduction can be carried out with a suitable chemical reducing agent or by catalytic hydrogenation. For example, the reduction is conveniently carried out by hydrogenating under conditions similar to those described above for reducing compounds of Formula I in which $R^1$ is nitro (for further details see Example 13, infra.).

Compounds of Formula 3 in which $R^1$ is —NHC(O)$R^5$ in which $R^5$ is as defined in the Summary of the Invention with respect to Formula I can be prepared by reacting a compound of Formula 3 in which $R^1$ is amino with an appropriate acylating agent (e.g., acyl halides such as acetyl chloride, benzoyl chloride, nicotinoyl chloride, etc.). The reaction is carried out in a suitable solvent (e.g., methylene chloride, THF, pyridine, water, any appropriate mixture of suitable solvents, etc., preferably pyridine) at −10° C. to 40° C., typically at 15° C. to 35° C. and preferably at approximately 25° C., and requires 0.5 to 8 hours.

Compounds of Formula 3 in which $R^1$ is —NHSO$_2$R$^5$ in which $R^5$ is as defined in the. Summary of the Invention with respect to Formula I can be prepared by reacting a compound of Formula 3 in which $R^1$ is amino with an appropriate sulfonyl halide (e.g., 4-trifluorobenzenesulfonyl chloride, 1-pyrrolidinesulfonyl chloride, 2-thiophenesulfonyl chloride, etc.). The reaction is carried out in by proceeding as described above for preparing compounds of Formula I in which $R^1$ is —NHSO$_2$R$^5$ from corresponding compounds in which $R^1$ is amino (for further details see Example 14, infra.).

Compounds of Formula 3 in which $R^1$ is —NHC(S)NHR$^5$ or —NHC(O)NHR$^5$ can be prepared by reacting a compound of Formula 3 in which $R^1$ is amino with an isothiocyanate of the formula $R^5$NC(S) or an isocyanate of the formula $R^5$C(O), in which $R^5$ is as defined in the Summary of the Invention with respect to Formula I. The reaction is carried out by proceeding as described above for preparing compounds of Formula I in which $R^1$ is —NHC(S)NHR$^5$ from corresponding compounds in which $R^1$ is amino (for further details see Example 15, infra.).

Compounds of Formulae 4 and 5:

Compounds of Formula 4 are commercially available or can be made by processes known to those of ordinary skill in the art. For example, a compound of Formula 4 in which t is 3, u is 1, two adjacent $R^1$ radicals form ethylenedioxy, a third $R^1$ radical is chloro and $R^2$ is chloro (i.e., 6,7-dichloro-1,4-benzodioxan) can be prepared by halogenating 1,4-benzodioxan. The halogenation is carried out with a suitable halogenating agent (e.g., N-chlorosuccinimide, chlorine, 1,3-dichloro-5,5-dimethylhydantoin, etc.) in a suitable solvent (e.g., acetic acid, DMF, acetonitrile, any appropriate mixture of suitable solvents, etc., preferably acetic acid) at approximately 120° C. (for further details see Example 6, infra.).

Compounds of Formula 4 in which $R^1$ is —NHSO$_2$R$^5$, in which $R^5$ is as defined in the Summary of the Invention with respect to Formula I, can be prepared by reacting a compound of Formula 4 in which $R^1$ is amino with an appropriate sulfonyl halide (e.g., 4-trifluorobenzenesulfonyl chloride, 1-pyrrolidinesulfonyl chloride, 3-(5-trifluoromethyl-1-methylpyrazol-3-yl)-2-thiophenesulfonyl chloride, etc.). The reaction is carried out in the presence of a suitable base (e.g., triethylamine, diisopropylethylamine, etc.) and in a suitable solvent (e.g., THF, 1-methyl-2-pyrrolidinone, DMF, dichloroethane, any appropriate mixture of suitable solvents, etc., preferably THF) at approximately reflux, requiring approximately 48 hours.

Compounds of Formula 5 can be prepared by reacting a protected acid of the formula L(CH$_2$)$_n$COOH (e.g., tert-butyl ω-halo(C$_{2-6}$)alkanoate) deprotecting and then activating (e.g., convert to the corresponding acid halide).

EXAMPLE 1

Methyl 6-methoxy-1,3-benzodioxole-5-carboxylate

A mixture of methyl 1,3-benzodioxole-5-carboxylate (9.3 g, 51 mmol) acetic acid (25 mL) and fuming nitric acid (50 mL) was stirred approximately 15 minutes and then poured into ice-water (600 mL). The mixture was allowed to stand 1 hour in an ice-bath and the solids were collected, stirred with water and recollected to give methyl 6-nitro-1,3-benzodioxole-5-carboxylate.

A mixture of the methyl 6-nitro-1,3-benzodioxole-5-carboxylate, 5% palladium on carbon (1.5 g), ethyl acetate (180 mL) and methanol (80 mL) was stirred 3 hours under a hydrogen atmosphere (15 psi). The mixture was filtered and concentrated and the residue was recrystallized from cyclohexane (200 mL) to give methyl 6-amino-1,3-benzodioxole-5-carboxylate (6.3 g, 32 mmol), m.p. 107°–108° C.

A mixture of methyl 6-amino-1,3-benzodioxole-5-carboxylate (6.3 g, 32 mmol), concentrated sulfuric acid (7 mL) and water (35 mL) was cooled in an ice-bath and then a mixture of sodium nitrite (2.3 g, 33 mmol) and water (15 mL) was added. The mixture was diluted with 50 mL of water and added to a boiling solution of cupric sulfate pentahydrate (35 g, 140 mmol) and water (75 mL). The mixture was heated 10 minutes at boiling and then cooled in an ice-bath and extracted with diethyl ether (3×). The combined extracts were washed with water (4×) and brine (1×), dried. (K$_2$CO$_3$) and concentrated. The residue was purified by column chromatography eluting with hexane/ethyl acetate (98:2–97:3) to give methyl 6-hydroxy-1,3-benzodioxole-5-carboxylate (2.7 g, 14 mmol), m.p. 100°–101° C.

A mixture of methyl 6-hydroxy-1,3-benzodioxole-5-carboxylate (2.7 g, 14 mmol), sodium hydride (456 mg, 19 mmol, 760 mg of a 60% dispersion in mineral oil), iodomethane (1.9 g, 13 mmol) and DMF (approximately 35 mL) was stirred 2 hours. The mixture was poured into ice-water and the mixture was extracted with diethyl ether (2×). The combined extracts were washed with water (3×) and brine (1×) and concentrated to give methyl 6-methoxy-1,3-benzodioxole-5-carboxylate (3 g, 14 mmol), m.p. 74°–75° C.

EXAMPLE 2

Ethyl 2-methoxy-5-phenoxybenzoate

A mixture of methyl 5-iodo-2-methoxybenzoate (14 g, 48 mmol), 30% aqueous sodium hydroxide (40 mL) and methanol (200–300 mL) was allowed to stand approximately 2 hours and th&n heated 5 minutes at reflux. The mixture was concentrated and the residue was stirred with water (500 mL). The mixture was treated with 10% hydrochloric acid (200 mL) and then cooled to 10° C. and the solids were collected and dried under vacuum at 90° C. to give 5-iodo-2-methoxybenzoic acid (13.4 g, 48 mmol), m.p. 150°–152° C.

A mixture of 5-iodo-2-methoxybenzoic acid (13.4 g, 48 mmol), acetyl chloride (1 mL) and ethanol (50 mL) was heated 4 hours with stirring at reflux. The mixture was concentrated and the residue was dissolved in diethyl ether. The solution was poured into ice-cold saturated sodium bicarbonate and the organic phase was washed with brine, dried ($K_2CO_3$), filtered and concentrated to give ethyl 5-iodo-2-methoxybenzoate (13.5 g, 44 mmol) as an oil.

A mixture of ethyl 5-iodo-2-methoxybenzoate (4.1 g, 13.4 mmol), sodium phenoxide (1.7–1.8 g, 15 mmol), copper(I) oxide (1.1 g, 7.5 mmol) and dimethylacetamide (approximately 15 mL) was heated 4 hours with stirring at 180° C. The mixture was filtered, diluted with water and extracted with pentane/diethyl ether (7:3, 2× 100 mL). The combined extracts were washed with dilute sodium hydroxide (3×) and water (1×), dried ($K_2CO_3$), filtered and concentrated. The residue was dried ($P_2O_5$) under vacuum to give crude product (1.17 g) which was combined with crude product (2.4 g) similarly prepared from methyl 5-iodo-2-methoxybenzoate (6 g, 19.6 mmol). The combined crude product was purified by column chromatography eluting with hexane/acetone (96:4) to give ethyl 2-methoxy-5-phenoxybenzoate (2 g, 7.3 mmol), m.p. 52°–52° C.

EXAMPLE 3

6-Methoxy-1,3-benzodioxole-5-carboxylic Acid

A mixture of methyl 6-methoxy-1,3-benzodioxole-5-carboxylate (3 g, 14 mmol), prepared as in Example 1, 20% sodium hydroxide (50 mL) and ethanol (25 mL) was heated 1 hour at reflux and then diluted with water, washed with diethyl ether (2×), treated with concentrated hydrochloric acid and cooled in an ice-bath. The solids were collected, washed with water (2×) and dried under vacuum at 70° C. to give 6-methoxy-1,3-benzodioxole-5-carboxylic acid (2.3 g, 12 mmol), m.p. 151° C.

Proceeding similarly as in Example 3 with different starting materials gave 2-methoxy-5-phenoxybenzoic acid.

EXAMPLE 4

N-Methoxy-N-methyl-5-chloro-2-methoxybenzamide

The following is the preparation of a compound of Formula 17 in which t is 1, u is 1, $R^1$ is chloro at the B-position and $R^2$ is methoxy.

A mixture of 5-chloro-o-anisic acid (50 g, 0.27 mol), oxalyl chloride (23 mL, 0.27 mol) and methylene chloride was stirred 1 hour at approximately 25° C. and then treated with DMF (2 drops). The mixture was stirred an additional hour, heated 45 minutes at reflux and then concentrated. The residue was dissolved in THF and the solution was reconcentrated. The residue was dissolved in THF-(approximately 200 mL) and the solution was added in a thin stream to a mixture of triethylamine (96 mL, 0.7 mol), N,O-dimethylhydroxylamine hydrochloride (26.3 g, 0.27 mol) and methylene chloride (approximately 300 mL). After an exothermic reaction had ensued, the mixture was allowed to cool to 25° C. and stirred approximately 16 hours. The mixture was filtered, concentrated and then partitioned between ethyl acetate and water. The organic layer was separated, washed with water (2×), sodium bicarbonate. (2×), 2% hydrochloric acid (1×) and brine (1×), dried ($K_2CO_3$), filtered and concentrated to give N-methoxy-N-methyl-5-chloro-2-methoxy-benzamide (52.3 g, 0.23 mmol), m.p. 80°–83° C.

Proceeding similarly as in Example 4 with different starting materials gave the following compounds of Formula 17:
N-methoxy-N-methyl-2-methoxybenzamide,
N-methoxy-N-methyl-2,5-dichlorobenzamide,
N-methoxy-N-methyl-2,5-dimethoxybenzamide,
N-methoxy-N-methyl-2,4,5-trimethoxybenzamide,
N-methoxy-N-methyl-5-chloro-2-ethoxybenzamide,
N-methoxy-N-methyl-4-chloro-2-ethoxybenzamide,
N-methoxy-N-methyl-4-methoxybiphenyl-3-carboxamide,
N-methoxy-N-methyl-4-chloro-2-methoxybenzamide,
N-methoxy-N-methyl-2-methoxy-1-naphthalenecarboxamide,
N-methoxy-N-methyl-3-methoxynaphthalenecarboxamide,
N-methoxy-N-methyl-6-methoxy-2-naphthalenecarboxamide,
N-methoxy-N-methyl-2-methoxy-5-phenoxybenzamide,
N-methoxy-N-methyl-2-benzyloxy-5-chlorobenzamide,
N-methoxy-N-methyl-3,5-dichloro-2-methoxybenzamide,
N-methoxy-N-methyl-6-bromo-2-methoxy-1-naphthalenecarboxamide and
N-methoxy-N-methyl-6-methoxy-1,3-benzodioxole-5-carboxamide.

EXAMPLE 5

N-Methoxy-N-methyl-5-chloro-2,4-dimethoxybenzamide

The following is the preparation of a compound of Formula 17 in which t is 2, u is 1, $R^1$ is chloro and methoxy at the β- and γ-positions, respectively, and $R^2$ is methoxy.

A mixture of N-methoxy-N-methyl-2,4-dimethoxybenzamide (7.2 g, 32 mmol), prepared as in Example 4, N-chlorosuccinimide (4.8 mL, 36 mmol) and acetonitrile (100 mL) was heated 16 hours at 50° C. The mixture was concentrated and the residue was partitioned between ethyl acetate (300 mL) and saturated sodium bicarbonate (150 mL). The mixture was filtered and the organic layer was separated, washed with water (4×) and brine (1×), dried ($K_2CO_3$), filtered through a short column of silica-gel and concentrated to give N-methoxy-N-methyl-5-chloro-2,4-dimethoxybenzamide (5.3 g, 20 mmol), m.p. 97°–99° C.

EXAMPLE 6

6,7-Dichloro-1,4-benzodioxan

The following is the preparation of a compound of Formula 4 in which t is 3, u is 1, two adjacent $R^1$ radicals form ethylenedioxy, a third $R^1$ radical is chloro and $R^2$ is chloro.

A mixture of 1,4-benzodioxan (59.5 g, 0.437 mol) N-chlorosuccinimide (121.5 g, 0.91 mol) and acetic acid (150 mL) was heated 30 minutes with stirring at 120° C. and then allowed to cool to approximately 25° C. and diluted with water (400 mL). The solids were collected, washed with water, stirred with a mixture of ethyl acetate (900 mL) and toluene (250 mL), recollected, stirred with water and dried at 60° C. to give 6,7-dichloro-1,4-benzodioxan (16 g, 78 mmol), m.p. 149°–151° C. The ethyl acetate/toluene solution was concentrated to approximately 200 mL, diluted with methanol (200 mL) and cooled in an ice-bath. The solids were collected, washed with cold methanol (200 mL) and dried at 60°–70° to give additional 6,7-dichloro-1,4-benzodioxan (43.5 g, 212 mmol), m.p. 148°–150° C.

EXAMPLE 7

5-Chloro-1-(5-chloro-2-methoxyphenyl)-1-pentanone

The following is the preparation of a compound of Formula 3 in which L is chloro, n is 4, t is 1, u is 1, $R^1$ is chloro at the β-position, $R^2$ is methoxy and $R^6$ and $R^7$ form oxo.

A mixture of 5-chloro-1-iodobutane (30 g, 137.6 mmol), ether (300 mL) and pentane (500 mL) was cooled to approximately –65° C. and then tert-butyllithium (1.7M, 160 mL, 0.27 moles) was added over 30 minutes such that the reaction mixture remained below approximately –55° C. The mixture was cooled 1 hour with stirring at –65° C. to –60° C. and then N-methoxy-N-methyl-5-chloro-2-methoxybenzamide (25 g, 0.11 mol), prepared as in Example 4, in THF (approximately 80 mL) was added. The mixture was diluted with additional ether (300 mL), allowed to warm to 10° C. and then combined with saturated ammonium chloride. The organic layer was separated, dried ($K_2CO_3$), filtered and concentrated. The residue was purified by column chromatography eluding with hexane/ethyl acetate (9:1 to 85:15) to give 5-chloro-1-(5-chloro-2-methoxy-phenyl)-1-pentanone, m.p. 52°–54° C.

Proceeding similarly as in Example 7 with different starting materials gave the following compounds of Formula 3:

5-chloro-1-(2-methoxyphenyl)-1-pentanone,
5-chloro-1-(2,5-dichlorophenyl)-1-pentanone,
5-chloro-1(2,5-dimethoxyphenyl)-1-pentanone,
5-chloro-1-(4-methoxy-biphenyl-3-yl)-1-pentanone,
5-chloro-1-(2,4,5-trimethoxyphenyl)-1-pentanone,
5-chloro-1-(5-chloro-2-ethoxyphenyl)-1-pentanone,
5-chloro-1-(4-chloro-2-ethoxyphenyl)-1-pentanone,
5-chloro-1-(4-chloro-2-methoxyphenyl)-1-pentanone,
5-chloro-1-(2-methoxynaphthalen-1-yl)-1-pentanone,
5-chloro-1-(3-methoxynaphthalen-2-yl)-1-pentanone,
5-chloro-1-(6-methoxynaphthalen-2-yl)-1-pentanone,
5-chloro-1-(2-methoxy-5-phenoxyphenyl)-1-pentanone,
5-chloro-1-(2-benzyloxy-5-chlorophenyl)-1-pentanone,
5-chloro-1-(3,5-dichloro-2-methoxyphenyl)-1-pentanone,
5-chloro-1-(5-chloro-2,4,-dimethoxyphenyl)-1-pentanone,
5-chloro-1-(6-bromo-2-methoxynaphthalen-1-yl)-1-pentanone,
5-chloro-1-(2-methoxy-4,5-methylenedioxyphenyl)-1-pentanone and
6-bromo-1-(5-chloro-2-methoxyphenyl)-1-hexanone.

EXAMPLE 7A

5-Chloro-1-(2,4,6-trimethoxyphenyl)-1-pentanone

The following is the preparation of a compound of Formula 3 in which L is chloro, n is 4, t is 2, u is 1, $R^1$ is methoxy at the α- and γ-positions, $R^2$ is methoxy and $R^6$ and $R^7$ form oxo.

The following is the preparation of a compound of Formula 3 in which A mixture of aluminum chloride (22.6 g, 170 mmol), 5-chlorovaleryl chloride (26.4 g, 170 mmol), and 1,2-dichloroethane (200 mL) was stirred for 30 minutes, and then filtered. The filtrate was added to a solution of trimethoxybenzene (26.7 g, 158 mmol) in 1,2-dichloroethane (100 mL); with reaction mixture warming spontaneously to approximately 50° C. Thin layer chromatography of a water-quenched sample taken after four hours showed complete reaction. The reaction mixture was poured over ice, and ethyl acetate was added to extract the product. The ethyl acetate phase was washed twice with water and once with brine, then dried over anhydrous sodium sulfate. The solution was filtered and the solvent removed, then the resulting oil was dissolved in a warm 20% solution of ethyl acetate in hexane (250 mL). The solution was allowed to crystallize at room temperature for five hours, then at 4° C. for one hour. Filtration, washing the crystals with 10% ethyl acetate in hexane, and air-drying afforded 5-chloro-1-(2,4,6-trimethoxyphenyl)-1-pentanone, 34 g (83% yield), m.p. 53°–55° C.

EXAMPLE 8

7-Bromo-1-(5-chloro-2-methoxyphenyl)-1-heptanone

The following is the preparation of a compound of Formula 3 in which n is bromo, n is 6, t is 1, u is 1, $R^1$ is chloro at the β-position, $R^2$ is methoxy and $R^6$ and $R^7$ form oxo.

A mixture of 7-bromoheptanoic acid (7.6 g, 36.4 mmol), oxalyl chloride (4 mL, 45.8 mmol) and 1,2-dichloroethane (80 mL) was stirred 45 minutes at approximately 25° C. and an additional 45 minutes at approximately 45° C. and then concentrated. The residue was stirred approximately 16 hours with a mixture of aluminum chloride (4.3 g, 32 mmol), 4-chloroanisole (4 g, 28 mmol) and dichloroethane (approximately 200 mL). The mixture was then poured over cold dilute hydrochloric acid and diluted with methylene chloride. The organic layer was separated, washed with water (3×) and dried ($K_2CO_3$). The residue was purified by column chromatography eluting with hexane/ethyl acetate (95:5) to give 7-bromo-1-(5-chloro-2-hydroxyphenyl)-1-heptanone (250 mg, 0.78 mmol), m.p. 79°–80° C. and 7-bromo-1-(5-chloro-2-methoxyphenyl)-1-heptanone (3.3 g, 9.9 mmol) as an oil.

Proceeding similarly as in Example 8 with different starting materials gave the following compounds of Formula 3:

6-bromo-1-(2,4-dimethoxyphenyl)-1-hexanone as an oil;
6-bromo-1-(5-phenyl-2-methoxyphenyl)-1-hexanone as an oil;
5-chloro-1-(5-phenyl-2-methoxyphenyl)-1-pentanone as an oil;
6-bromo-1-(2-hydroxy-4-methoxyphenyl)-1-hexanone, m.p. 57°–58° C.;
5-chloro-1-(2,3-dichloro-5,6-ethylenedioxyphenyl)-1-pentanone, m.p. 54°–55° C.;
4-chloro-1-(5-chloro-2-hydroxyphenyl)-1-butanone and 4-chloro-1-(5-chloro-2-methoxyphenyl)-1-butanone as a mixture;
6-bromo-1-(5-chloro-2-hydroxyphenyl)-1-hexanone and 6-bromo-1-(5-chloro-2-methoxyphenyl)-1-hexanone as a mixture; and
N-[4-(5-chloropentanoyl)-2,5-dimethoxyphenyl]-4-chlorobenzenesulfonamide, m.p. 116°–119° C.

EXAMPLE 9

5-Chloro-1-(2,3-ethylenedioxyphenyl)-1-pentanone

The following is the preparation of a compound of Formula 3 in which L is chloro, n is 4, t is 2, u is 0, two adjacent $R^1$ radicals form α,β-ethylenedioxy and $R^6$ and $R^7$ form oxo.

A mixture of 5-chloro-1-(5,6-ethylenedioxy-2,3-dichlorophenyl-1-pentanone (4.9 g, 15.2 mmol), prepared as in Example 8, 10% palladium on carbon (900 mg), 1.0% sodium hydroxide (40–50 mL) and methanol (200 mL) was stirred 24 hours under a hydrogen atmosphere. The mixture was filtered and concentrated and the residue was dissolved in water. The solution was extracted with ether/hexane (8:2; 1× 100 mL) and the extract was concentrated. The residue was purified by column chromatography eluting With hexane/ethyl acetate (9:1) to give 5-chloro-1-(2,3-ethylenedioxyphenyl)-1-pentanone (2.1 g, 8.3 mmol), m.p. 32°–38° C.

EXAMPLE 10

5-Chloro-1-(5-chloro-2-methoxyphenyl)-1,1-ethylenedioxypentane

The following is the preparation of a compound of Formula 3 in which L is chloro, n is 4, t is 1, u is 1, $R^1$ is chloro at the β-position, $R^2$ is methoxy and $R^6$ and $R^7$ form ethylenedioxy.

A mixture of 5-chloro-1-(5-chloro-2-methoxyphenyl)-1-pentanone (2 g, 7.66 mmol), prepared as in Example 7, ethylene glycol (1.25 g, 20 mmol), 2-napthalenesulfonic acid (50 mg, 0.24 mmol) and toluene (approximately 80 mL) was heated 4–5 hours at reflux (removing water with a Dean-Stark trap) and then additional ethylene glycol (1 g, 16 mmol) was added. The mixture was heated approximately 16 hours at reflux and then washed with saturated sodium bicarbonate, water (3×) and brine (1×), dried ($K_2CO_3$), filtered and concentrated to give 5-chloro-1-(5-chloro-2-methoxyphenyl)-1,1-ethylenedioxypentane (2.23 g, 7.31 mmol) as an oil.

Proceeding similarly with different starting materials gave the following compounds of Formula 3:

5-(5-chloro-1,1-ethylenedioxypentyl)-1,4-benzodioxan as an oil; and 4-chloro-1-(5-chloro-2-hydroxyphenyl)-1,1-ethylenedioxybutane as an oil.

EXAMPLE 11

4-Chloro-1-(5-chloro-2-methoxyphenyl)-1,1-ethylenedioxybutane

The following is the preparation of a compound of Formula 3 in which L is chloro, n is 3, t is 1, u is 1, $R^1$ is chloro at the β-position, $R^2$ is methoxy and $R^6$ and $R^7$ form ethylenedioxy.

A mixture of 4-chloro-1-(5-chloro-2-hydroxyphenyl)-1,1-ethylenedioxybutane (0.86 g, 2.5 mmol) sodium hydride (0.18 g, 4.5 mmol in mineral oil) and DMF (3 mL) was stirred 30 minutes. The mixture was cooled to approximately 0° C. and dimethyl sulfate (0.44 g, 3.5 mmol) was added. The mixture was heated 4 hours with stirring at approximately 25° C. and then poured into ice cold water. The mixture was extracted with ether/pentane (7:3) and the extract concentrated to give 4-chloro-1-(5-chloro-2-methoxyphenyl)-1,1-ethylenedioxybutane (0.85 g, 2.4 mmol).

Proceeding similarly as in Example 11 with different starting materials gave 5-chloro-1-(2-benzyloxy-5-chlorophenyl)-1-pentanone.

EXAMPLE 12

5-Chloro-1-(2,4-dimethoxy-5-nitrophenyl)-1-pentanone

The following is the preparation of a compound of Formula 3 in which L is chloro, n is 4, t is 2, u is 1, $R^1$ is nitro and methoxy at the β- and γ-positions, respectively, $R^2$ is methoxy and $R^6$ and $R^7$ form oxo.

A mixture of 5-chloro-1-(2,4-dimethoxyphenyl)-1-pentanone (11.07 g, 3.12 mmol), prepared as in Example 7, and acetic anhydride (75 mL) was cooled at 5°–6° C. and then copper(II) nitrate hemipentahydrate (6.25 g, 25.9 mmol) was added. The mixture was cooled approximately 6 hours with stirring at 15°–16° C. filtered, poured into water, stirred with potassium carbonate and then extracted with ethyl acetate. The extract was washed with dilute ammonium hydroxide and then brine, dried ($Na_2SO_4$), filtered and concentrated. The residue was recrystallized from ethyl acetate to give 5-chloro-1-(2,4-dimethoxy-5-nitrophenyl)-1-pentanone (8.81 g, 29.2 mmol), m.p. 93°–95° C.

Proceeding similarly as in Example 12 with different starting materials gave the following compounds of Formula 3:

substituting 5-(5-chloro-1,1-ethylenedioxypentyl)-1,4-benzodioxan gave 5-(5-chloro-1,1-ethylenedioxypentyl-7-nitro-1,4-benzodioxan, m.p. 74°–76° C.; and substituting 5-chloro-1-(2-methoxyphenyl)-1-pentanone gave 5-chloro-1-(2-methoxy-3-nitrophenyl)-1-pentanone as an oil and 5-chloro-1-(2-methoxy-5-nitrophenyl)-1-pentanone, m.p. 57°–58° C.

EXAMPLE 12A

5-Chloro-1-(3-nitro-2,4,6-trimethoxyphenyl)-1-pentanone

The following is the preparation of a compound of Formula 3 in which L is chloro, n is 4, t is 3, u is 1, $R^1$ is nitro at the β-position and methoxy at the α- and γ-positions, $R^2$ is methoxy and $R^6$ and $R^7$ form oxo.

A mixture of 5-chloro-1-(2,4,6-trimethoxyphenyl)-1-pentanone (41.5 g, 160 mmol), prepared as in Example 7A, acetic acid (150 mL) and acetic anhydride (70 mL) was cooled at 8° C. and then copper(II) nitrate hemipentahydrate (14 g, 60.2 mmol) was added. The mixture was cooled approximately 3 hours with stirring at 15°–18° C.; then additional copper(II) nitrate hemipentahydrate (5.5 g, 23.6 mmol) was added. The mixture was cooled a further approximately 4 hours with stirring at 15°–18° C.; then filtered, and the filtrate stored at 5° C. for 16 hours. The filtrate was then poured into an ice/water mixture, and potassium carbonate added with stirring until the mixture remained alkaline. The mixture was then extracted with ethyl acetate. The extract was washed with dilute ammonium hydroxide and then brine, dried ($Na_2SO_4$), filtered and concentrated. The residue was purified by column chromatography eluting with hexane/methylene chloride/methanol (60:40:1) to give 5-chloro-1-(3-nitro-2,4,6-trimethoxyphenyl)-1-pentanone (8.4 g, 25 mmol) as an oil.

EXAMPLE 13

5-Chloro-1-(5-amino-2,4-dimethoxyphenyl)-1-pentanone

The following is the preparation of a compound of Formula 3 in which L is chloro, n is 4, t is 2, u is 1, $R^1$ is amino and chloro at the β- and γ-positions, respectively, $R^2$ is methoxy and $R^6$ and $R^7$ form oxo.

A mixture of 5-chloro-1-(2,4-dimethoxy-5-nitrophenyl)-1-pentanone (2.9 g, 9.6 mmol), prepared as in Example 12, 10% palladium on carbon (650 mg) and THF (approximately 170 mL) was stirred 3 hours under a hydrogen atmosphere (15 psi). The mixture was filtered and concentrated and the residue was purified by column chromatography eluting with hexane/ethyl acetate (60:40) to give 5-chloro-1-(5-amino-2,4-dimethoxyphenyl)-1-pentanone (1.9 g, 7 mmol), m.p. 87°–88° C.

Proceeding similarly as in Example 13 with different starting materials gave 7-amino-5-(5-chloro-1,1-ethylenedioxypentyl)-1,4-benzodioxan as an oil; and (using the material from Example 12A) gave 5-chloro-1-(3-amino-2,4,6-trimethoxyphenyl)-1-pentanone (8.4 g, 25 mmol) as an oil.

EXAMPLE 14

N-[5-(5-Chloropentanoyl)-2,4-dimethoxyphenyl]-4-trifluoromethylbenzenesulfonamide The following is the preparation of a compound of Formula 3 in which L is chloro, n is 4, t is 2, u is 1, $R^1$ is 4-trifluoromethylphenylsulfonylamino and methoxy at the β- and γ-positions, respectively, $R^2$ is methoxy and $R^6$ and $R^7$ form oxo.

A mixture of 1-(5-amino-2,4-dimethoxyphenyl)-5-chloro-1-pentanone (0.54 g, 2 mmol), prepared as in Example 13, 4-trifluoromethylbenzenesulfonyl chloride (0.51 g, 2.1 mmol) triethylamine (0.25 g, 2.5 mmol) and THF (approximately 50 mL) was stirred 16 hours at approximately 25° C. The mixture was concentrated and the residue was partitioned between ethyl acetate and dilute ammonium hydroxide. The organic layer was washed with water (1×) and then brine (1×), dried ($K_2CO_3$), filtered and concentrated to give N-[5-(5-chloropentanoyl)-2,4-dimethoxyphenyl]-4-trifluoromethylbenzenesulfonamide (0.8 g, 1.7 mmol), m.p. 150°–153° C.

Proceeding similarly as in Example 14 with different starting materials gave the following compounds of Formula 3.

N-[3-(5-chloropentanoyl)-4-methoxyphenyl]acetamide,
N-[2-chloro-4-(5-chloro-pentanoyl)-5-methoxyphenyl] acetamide,
N-{4-[5-(5-chloropentanoyl)-2,4-dimethoxyphenylsulfamoyl]phenyl}acetamide,
N-[3-(5-chloropentanoyl)-4-methoxyphenyl]benzamide,
N-[3-(5-chloropentanoyl)-4-methoxyphenyl]-2-chlorobenzamide,
N-[5-(5-chloropentanoyl)-2,4-dimethoxyphenyl]pyridine-4-carboxamide,
N-[3-(5-chloropentanoyl)-4-methoxyphenyl]benzenesulfonamide,
N-[3-(5-chloro-pentanoyl)-4-methoxyphenyl]-1-pyrrolesulfonamide,
N-[5-(5-chloropentanoyl)-2,4-dimethoxyphenyl]methanesulfonamide,
N-[5-(5-chloropentanoyl)-2,4-dimethoxyphenyl]benzenesulfonamide,
N-[5-(5-chloropentanoyl)-2,4-dimethoxyphenyl]-4-toluenesulfonamide, m.p. 152°–153° C.
N-[5-(5-chloropentanoyl)-2,4-dimethoxyphenyl]biphenylsulfonamide,
N-[5-(5-chloropentanoyl)-2,4-dimethoxyphenyl]-1-pyridinesulfonamide,
N-[5-(5-chloropentanoyl)-2,4-dimethoxyphenyl]-1-thiophenesulfonamide,
N-[3-(5-chloropentanoyl)-4-methoxyphenyl]-4-chlorobenzenesulfonamide,
N-[5-(5-chlorapentanoyl)-2,4-dimethoxyphenyl]-2-naphthalenesulfonamide,
N-[5-(5-chloropentanoyl)-2,4-dimethoxyphenyl]-4-aminobenzenesulfonamide,
N-[5-(5-chloropentanoyl)-2,4-dimethoxyphenyl]-4-cyanobenzenesulfonamide,
N-[5-(5-chloropentanoyl)-2,4-dimethoxyphenyl]-4-nitrobenzenesulfonamide,
N-[5-(5-chloropentanoyl)-2,4-dimethoxyphenyl]-2-chlorobenzenesulfonamide,
N-[5-(5-chloropentanoyl)-2,4-dimethoxyphenyl]-3-chlorobenzenesulfonamide,
N-[5-(5-chloropentanoyl)-2,4-dimethoxyphenyl]-4-chlorobenzenesulfonamide,
N-[3-(5-chloropentanoyl)-4-methoxyphenyl]-3,4-dimethoxybenzenesulfonamide,
N-[5-(5-chloropentanoyl)-2,4-dimethoxyphenyl]-4-methoxybenzenesulfonamide,
N-[5-(5-chloropentanoyl)-2,4-dimethoxyphenyl]-4-(prop-2-yl)benzenesulfonamide,
N-[3-(5-chloropentanoyl)-4-methoxyphenyl]-N-phenylsulfonylbenzenesulfonamide,
N-[5-(5-chloropentanoyl)-2,4-dimethoxyphenyl]-2,4-difluorobenzenesulfonamide,
N-[5-(5-chloropentanoyl)-2,4-dimethoxyphenyl]-3,4-difluorobenzenesulfonamide,
N-[5-(5-chloropentanoyl)-2,4-dimethoxyphenyl]-5-chloro-2-thiophenesulfonamide,
N-[5-(5-chloropentanoyl)-2,4,6-trimethoxyphenyl]-4-trifluoromethylbenzenesulfonamide, m.p. 128°–130° C.
N-[5-(5-chloropentanoyl)-2,4-dimethoxyphenyl]-3-trifluoromethylbenzenesulfonamide,
N-[5-(5-chloropentanoyl)-2,4-dimethoxyphenyl]-5-pyrid-2-yl-2-thiophenesulfonamide,
N-[5-(5-chloropentanoyl)-2,4-dimethoxy-phenyl]-4-trifluoromethoxybenzenesulfonamide,
N-[5-(5-chloropentanoyl)-2,4-dimethoxyphenyl]-4-trifluoromethoxybenzenesulfonamide,
N-[5-(5-chloropentanoyl)-2,4-dimethoxyphenyl]-3,5-di(trifluoromethyl)benzenesulfonamide,
N-[3-(5-chloropentanoyl)-4,5-ethylenedioxyphenyl]-4-trifluoromethylbenzenesulfonamide,
N-[5-(5-chloro-1,1-ethylenedioxypentyl)-3,4-ethylenedioxyphenyl]-4-N-[5-(5-chloro-pentanoyl)-2,4-dimethoxyphenyl]-2-(5-trifluoromethylpyrid-2-yl-sulfonyl)-4-thiophenesulfonamide and
N-[5-(5-chloropentanoyl)-2,4-dimethoxyphenyl]-5-(5-trifluoromethylpyrid-2-yl-sulfonyl)-2-thiophenesulfonamide.

EXAMPLE 15

1-[5-(5-Chloropentanoyl)-2,4-dimethoxyphenyl]-3-(4-trifluoromethylphenyl)urea

The following is the preparation of a compound of Formula 3 in which L is chloro, n is 4, t is 2, u is 1, $R^1$ is 4-trifluorophenylureido and methoxy at the β- and γ-positions, respectively, $R^2$ is methoxy and $R^6$ and $R^7$ form oxo.

A mixture of 5-chloro-1-(5-amino-2,4-dimethoxyphenyl)-1-pentanone (0.27 g, 1 mmol), prepared as in Example 14, α,α,α-trifluoro-p-tolyl isocyanate (0.16 mL, 1.1 mmol), toluene (3 mL) and ethyl acetate (0.5 mL) was heated 10 minutes with stirring at approximately 50° C. The mixture was concentrated and the residue was recrystallized from hexane/ethyl acetate. The solids were collected and dried at 70° C. to give 1-[5-(5-chloropentanoyl)-2,4-dimethoxyphenyl]-3-(4-trifluoromethylphenyl)urea (0.43 g, 0.94 mmol), m.p. 154°–156° C.

Proceeding similarly as in Example 15 with different starting materials gave the following compounds of Formula 3:

1-[5-(5-chloropentanoyl)-2,4-dimethoxyphenyl]-3-prop-2-ylurea,

1-[5-(5-chloro-pentanoyl)-2,4-dimethoxyphenyl]-3-(3-trifluoromethylphenyl)urea and 1-[5-(5-chloropentanoyl)-2,4-dimethoxyphenyl]-3-(2-trifluoromethylphenyl)urea.

EXAMPLE 16

1,3,8-Triazaspiro[4.5]decane-2,4-dione

The following is the preparation of a compound of Formula 2 in which X is NH, Y is C(O), Z is C(O) and $R^3$ is hydro.

A mixture of tert-butyl 4-oxopiperidine-1-carboxylate (156 g, 0.783 mol), potassium cyanide (150 g, 2.3 mol), ammonium carbonate (370 g, 3.8 mol) and water (600 mL) was heated at approximately 50° C. The mixture was diluted with ethanol (750 mL) over 45 minutes and then 400 mL of solvent was removed by distilling 1 hour at 65°–85° C. The mixture was diluted with water (300 mL), heated to 85° C. diluted with additional water (500 mL), heated 30 minutes with stirring at 75° C. and then cooled to 10° C. The solids were collected, stirred with cold water (2×), recollected and dried at 60° C. to give tert-butyl 1,3,8-triaza-2,4-dioxo-8-spiro[4.5]decane-carboxylate (122 g, 0.45 mol).

A slurry of tert-butyl 1,3,8-triaza-2,4-dioxo-8-spiro[4.5]decanecarboxylate (122 g, 0.45 mol) and ethanol (400 mL) was heated at reflux and then dilute portionwise with a solution of hydrogen chloride in ethanol (prepared from acetyl chloride (160 mL) and ethanol (500 mL)). The mixture was heated 15 minutes at reflux and then cooled to approximately 25° C. and the solids were collected, washed with ethanol (approximately 130 mL) and dried to give 1,3,8-triaza-spiro[4.5]decane-2,4-dione hydrochloride, m.p. >280° C. (dec).

EXAMPLE 17

3,8-Diaza-1-oxaspiro[4.5]decane-2,4-dione

The following is the preparation of a compound of Formula 2 in which X is O, Y is C(O), Z is C(O) and $R^3$ is hydro.

A slurry of 1-benzyl-4-piperidone (53.3 g, 0.28 mol), sodium bisulfate (38.5 g, 0.32 mol), potassium cyanide (24.5 g, 0.38 mol) and water (200 mL) was stirred 1 hour and then combined with diethyl ether. The mixture was stirred 1 hour and the ether layer was separated, washed with water (2×) and brine (2×), dried ($K_2CO_3$), filtered and concentrated. The residue was crystallized from pentane/diethyl ether (3:1, approximately 400 mL) to give 1-benzyl-4-hydroxypiperidine-4-carbonitrile (45 g) as a crude material.

A mixture of crude 1-benzyl-4-hydroxypiperidine-4-carbonitrile (9.5 g), chlorosulfonyl isocyanate (6.4 g, 45 mmol) and toluene (200 mL) was stirred 1.5 hours at 25° C. 3.5 hours at reflux and then approximately 12 hours at 25° C. The mixture was concentrated and the residue was dissolved in ethanol (25 mL) and concentrated hydrochloric acid (5 mL). The solution was heated 7 days at reflux and concentrated. The residue was mixed with water (approximately 90 mL) and the solids were collected and dried to give 8-benzyl-3,8-diaza-1-oxaspiro[4.5]decane-2,4-dione (5.4 g, 21 mmol), m.p. 291°–294° C.

A mixture of 8-benzyl-3,8-diaza-1-oxaspiro[4.5]decane-2,4-dione (1.1 g, 4.2 mmol), 10% palladium on carbon (330 mg), acetic acid 10 mL, concentrated hydrochloric acid (2 mL) and water (20 mL) was hydrogenated approximately 12 hours at 15 psi of pressure. The mixture was filtered and concentrated and the residue was crystallized from isopropanol to give 3,8-diaza-1-oxaspiro[4.5]decane-2,4-dione (0.6 g, 2.9 mmol).

EXAMPLE 18

3-tert-Butyl-3,8-diaza-1-oxaspiro[4.5]decane-2-one

The following is the preparation of a compound of Formula 2 in which X is O, Y is $CH_2$, Z is C(O) and $R^3$ is tert-butyl.

A mixture of trimethylsulfoxonium iodide 127 g, 123 mmol), sodium hydride (3 g, 125 mmol) and DMSO (60 mL) was stirred 15–20 minutes under argon and then 1-benzyl-4-piperidone (22.7 g, 120 mmol) in DMSO. (60 mL) was added. The mixture was stirred 1 hour at 25° C. and 1 hour at 50° C. poured into water (1 L) and extracted with diethyl ether/hexane (1:1). The extract was dried ($Na_2SO_4$) and concentrated to give 6-aza-6-benzyl-1-oxaspiro[2.3] octane (21.4 g, 105 mmol). A mixture of 6-aza-6-benzyl-1-oxaspiro[2.3]octane (10 g, 49 mmol), tert-butylamine (20–30 mL, 190–285 mmol) and THF (approximately 5 mL) was heated 32 hours at 120° C. The mixture was concentrated and extracted with methylenechloride. The extract was dried ($Na_2SO_4$) and concentrated. The residue was stirred in heptane and then reisolated by filtration to give (tert-butyl) (1-benzyl-4-hydroxypiperidin-4-ylmethyl)amine (11.9 g, 43 mmol), m.p. 161°–162° C.

A mixture of (tert-butyl)(1-benzyl-4-hydroxypiperidin-4-ylmethyl)amine (11.9 g, 43 mmol), 1,1'-carbonyldiimidazole (8.4 g, 52 mmol) and THF (150 mL) was heated 3.5 hours at reflux. The mixture was cooled, poured into dilute hydrochloric acid and then washed with methylene chloride (2× 200 mL). The combined washes were extracted with dilute hydrochloric acid and the combined. aqueous layers were treated with sodium hydroxide and extracted with methylene chloride. The extract was dried ($Na_2SO_4$) and concentrated and the residue was recrystallized from heptane to give 8-benzyl-3-tert-butyl-3,8-diaza-1-oxaspiro[4.5]decane-2-one (9.98 g, 33 mmol), m.p. 110°–112° C.

A mixture of 8-benzyl-3-tert-butyl-3,8-diaza-1-oxaspiro [4.5]decane-2-one (9 g, 30 mmol), 10% palladium on carbon (0.9 g) and ethanol (100 mL) was stirred 6 to 7 hours under a hydrogen atmosphere (50 psi). The mixture was filtered and then concentrated to give crude 3-tert-butyl-3,8-diaza-1-oxaspiro[4.5]decane-2-one (7.2 g), m.p. 108°–111° C.

EXAMPLE 19

3-Methyl-1,3,8-triazaspiro[4.5]decane-2,4-dione

The following is the preparation of a compound of Formula 2 in which X is NH, Y is C(O), Z is C(O) and $R^3$ is methyl.

A mixture of tert-butyl 2,4-dioxo-1,3,8-triaza-8-spiro[4.5] decane-carboxylate (4.9 g, 18.2 mmol), dimethylsulfate (2.9 g, 23 mmol), potassium carbonate (10.8 g, 78.3 mmol) and DMF (60 mL) was stirred approximately 60 hours at 25° C. The mixture was concentrated and the residue was partitioned between ethyl acetate and water. The ethyl acetate layer was separated, washed with water (3×), dried ($Na_2SO_4$), filtered and concentrated to give tert-butyl 2,4-dioxo-3-methyl-1,3,8-triaza-8-spiro[4.5]decanecarboxylate (4.7 g, 16.6 mmol), m.p. 206°–208° C.

A mixture of tert-butyl 2,4-dioxo-3-methyl-1,3,8-triaza-8-spiro[4.5]decanecarboxylate (4.7 g, 16.6 mmol), hydrogen chloride (5 g, 13.7 mmol) and ethanol (90 mL) was heated approximately 10 minutes at reflux. The mixture was cooled in an ice-bath and the solids were collected, washed with ethanol and dried at 70° C. to give 3-methyl-1,3,8-triazaspiro[4.5]decane-2,4-dione hydrochloride (3.5 g, 15.9 mmol).

Proceeding similarly but with different starting materials gave N-[3-(2,4-dioxo-1,3,8-triazaspiro[4.5]decan-3-yl) propyl]-4-methoxybenzenesulfonamide as the trifluoroacetate salt.

EXAMPLE 19A 3-(1-Methylethyl)-1,3,8-triazaspiro[4.5]decane-2,4-dione

The following is the preparation of a compound of Formula 2 in which X is NH, Y is C(O), Z is C(O) and $R^3$ is isopropyl.

A mixture of tert-butyl 2,4-dioxo-1,3,8-triaza-8-spiro[4.5]decanecarboxylate (4.18 g, 15.5 mmol), 60% sodium hydride in oil (0.68 g, 17 mmol), and DMF (25 mL) was stirred approximately one hour at 25° C.; then 2-iodopropane (2.7 g, 16 mmol) was added and stirring was continued for three days. The solvent was removed under reduced pressure, and the residue was stirred with water (80 mL) for a few minutes. The insoluble solid was collected and purified by chromatography, eluting with ethyl acetate/hexane (60:40). tert-Butyl 2,4-dioxo-3-(1-methylethyl)-1,3,8-triaza-8-spiro[4.5]decanecarboxylate (0.66 g, 2.1 mmol), m.p. 206°–208° C. was obtained as fine needles.

The tert-butyl 2,4-dioxo-3-(1-methylethyl)-1,3,8-triaza-8-spiro[4.5]decanecarboxylate was deprotected in the manner described in Example 19 to give 3-(1-methylethyl)-1,3,8-triazaspiro[4.5]decane-2,4-dione as the hydrochloride salt, m.p. >285° C.

EXAMPLE 19B 3-(2,3-Dihydroxypropyl)-1,3,8-triazaspiro[4.5]decane-2,4-dione

The following is the preparation of a compound of Formula 2 in which X is NH, Y is C(O), Z is C(O) and $R^3$ is 2,3-dihydroxypropyl.

A mixture of tert-butyl 2,4-dioxo-1,3,8-triaza-8-spiro[4.5]decanecarboxylate (6.9 g, 25.6 mmol), 3-bromo-1,2-propanediol (4.4 g, 28 mmol), sodium iodide (1.5 g, 10 mmol), potassium carbonate (14 g) and DMF (25 mL) was stirred approximately 48 hours at 100° C. Additional 3-bromo-1,2-propanediol (1.5 g, 10 mmol) was added, and the stirring and heating continued for an additional 72 hours. After cooling, the mixture was filtered, the solvent removed from the filtrate under vacuum, and the residue was purified by chromatography eluting with ethyl acetate containing 0.5–1% acetic acid. The fractions containing the product were combined and concentrated, and the residue was treated with ethyl acetate to give tert-butyl 2,4-dioxo-3-(2,3-dihydroxypropyl)-1,3,8-triaza-8-spiro[4.5] decanecarboxylate (1.5 g, 4.4 mmol) as a white solid, m.p. 167°–170° C.

The tert-butyl 2,4-dioxo-3-(2,3-dihydroxypropyl)-1,3,8-triaza-8-spiro[4.5]decanecarboxylate was deprotected in the manner described in Example 19 to give 3-(2,3-dihydroxypropyl)-1,3,8-triazaspiro[4.5]decane-2,4-dione as the hydrochloride salt, m.p. 255°–256° C.

3-(2,3-Dihydroxypropyl)-1,3,8-triazaspiro[4.5]decane-2,4-dione may also be prepared by reaction of tert-butyl 2,4-dioxo-1,3,8-triaza-8-spiro[4.5]decanecarboxylate with an epihalohydrin to give tert-butyl 2,4-dioxo-3-(2,3-epoxypropyl)-1,3,8-triaza-8-spiro[4.5]decanecarboxylate, followed by hydrolysis of the epoxy group and deprotection.

Proceeding in a similar manner, using 2-iodoethanol, there was obtained 3-(2-hydroxyethyl)-1,3,8-triazaspiro[4.5]decane-2,4-dione as the hydrochloride salt, m.p. 267°–269° C.

Proceeding in a similar manner, using 3-(4-fluorophenyl)propyl methanesulfonate, there was obtained 3-(4-fluorophenyl)propyl-1,3,8-triazaspiro[4.5]decane-2,4-dione as the hydrochloride salt, m.p. 279°–283° C.

Proceeding in a similar manner, using 2,2-dimethyl-5-(4-toluenesulfonyloxymethyl)-1,3-dioxane (prepared by the method of Dubois et al. (1992), *Tetrahedron*, 47, 1001–1012), and cesium carbonate instead of potassium carbonate+sodium iodide, there was obtained 3-[2-(hydroxymethyl)-3-hydroxypropyl]-1,3,8-triazaspiro[4.5]decane-2,4-dione as the hydrochloride salt, m.p. 225°–228° C.

Other 3-substituted 1,3,8-triazaspiro[4.5]decane-2,4-diones may be prepared using the methods described.

EXAMPLE 20

4-Amino-1-[5-(5-chloro-2-methoxyphenyl)-5-oxopentyl]piperidine-4-carbonitrile

The following is the preparation of a compound of Formula 14 in which n is 4, t is 1, u is 1, $R^1$ is chloro at the β-position and $R^2$ is methoxy.

A mixture of 1-[5-(5-chloro-2-methoxyphenyl)-5,5-ethylenedioxypentyl]-4-piperidone (6.62 g, 18 mmol), potassium cyanide (1.4 g, 35.8 mmol), ammonium chloride (2.46 g, 37 mmol), ammonium hydroxide (14M, 4 mL, 56 mmol), water (25 mL) and methanol (120 mL) was heated 2 hours with stirring at approximately 25° C. and then 5 hours at 60° C. The mixture was concentrated and the residue was dissolved in ethyl acetate. The solution was washed with water (3×) and brine (1×), dried (MgSO$_4$) and concentrated to give 4-amino-1-[5-(5-chloro-2-methoxyphenyl)-5,5-ethylenedioxypentyl]piperidine-4-carbonitrile (5.2 g, 13.1 mmol).

EXAMPLE 21

4-Amino-1-[5-(5-chloro-2-methoxyphenyl)-5-oxopentyl]piperidine-4-carboxamide

The following is the preparation of a compound of Formula 16 in which n is 4, t is 1, u is 1, $R^1$ is chloro at the β-position and $R^2$ is methoxy.

A mixture of 4-amino-1-[5-(5-chloro-2-methoxyphenyl)-5,5-ethylenedioxypentyl]piperidine-4-carbonitrile (5.2 g, 13.1 mmol), prepared as in Example 20, water (1.6 mL) and sulfuric acid (41 mL) was warmed approximately 5 minutes on a steam bath and then cooled to 0° C. and diluted with water (150 mL). The mixture was washed with ethyl acetate (2×), cooled to 0° C. treated with potassium hydroxide, filtered, washed with chloroform and extracted with methylene chloride (4×). The combined extracts were dried (MgSO$_4$) and concentrated. The residue was recrystallized from ethyl acetate/hexane to give 4-amino-1-[5-(5-chloro-2-methoxyphenyl)-5-oxopentyl]piperidine-4-carboxamide (4.2 g, 11.4 mmol). Free base (135 mg, 0.367 mmol) was recrystallized from a solution of hydrogen chloride in ethanol to give 4-amino-1-[5-(5-chloro-2-methoxyphenyl)-5-oxo-pentyl]piperidine-4-carboxamide hydrochloride (65 mg, 0.16 mmol).

EXAMPLE 22

8-[5-(5-Chloro-2-methoxyphenyl)-5-oxopentyl]-2-thioxo-1,3,8-triazaspiro[4.5]decane-4-one The following is the preparation of a compound of Formula I in which n is 4, t is 1, u is 1, X is NH, Y is C(O), Z is C(S), $R^1$ is chloro at the β-position, $R^2$ is methoxy and $R^3$ is hydro.

A mixture of 4-amino-1-[5-(5-chloro-2-methoxyphenyl)-5-oxopentyl]-piperidine-4-carboxamide (0.36 g, 1 mmol), prepared as in Example 21, 1,1'-thiocarbonyldiimidazole (0.23 g, 1.3 mmol), and DMF (3 mL) was heated 5 hours at 50°–60° C. and then diluted with water. The mixture was extracted with ethyl acetate and the extract was dried (MgSO₄) and concentrated. The residue was purified by column chromatography eluting with methylene chloride/methanol+ammonium hydroxide (95:5) to give 8-[5-(5-chloro-2-methoxyphenyl)-5-oxopentyl]-2-thioxo-1,3,8-triazaspiro[4.5]decane-4-one (0.12 g, 0.29 mmol), m.p. 152°–154° C. (dec).

EXAMPLE 23

N-{5-[5-(2,4-Dioxo-1,3,8-triazaspiro[4.5]dec-8-yl)pentanoyl]-2,4-dimethoxyphenyl}-4-trifluoromethylbenzenesulfonamide The following is the preparation of a compound of Formula I in which n is 4, t is 2, u is 1, X is NH, Y is C(O), Z is C(O), $R^1$ is 4-trifluoromethylphenylsulfonylamino and methoxy at the β- and γ-positions, respectively, $R^2$ is methoxy and $R^3$ is hydro.

A mixture of N-[5-(5-chloropentanoyl)-2,4-dimethoxyphenyl]-4-trifluoromethylbenzenesulfonamide (0.8 g, 1.7 mmol), prepared as in Example 14, 1,3,8-triazaspiro[4.5]decane-2,4-dione hydrochloride (0.55 g, 2.7 mmol), prepared as in Example 16, sodium iodide (0.4 g, 2.7 mmol), triethylamine (0.5 g, 5 mmol) in DMF (approximately 5 mL) was heated 16 hours at 115° C. The mixture was concentrated and the residue was stirred with water and the solids were collected, dried and purified by column chromatography eluting with methylene chloride/methanol+ammonium hydroxide (95:5) to give N-{5-[5-(2,4-dioxo-1,3,8-triazaspiro[4.5]dec-8-yl)pentanoyl]-2,4-dimethoxyphenyl}-4-trifluoromethylbenzenesulfonamide (0.4 g, 0.65 mmol), m.p. 226° C. The free base was recrystallized from a solution of hydrogen chloride in ethanol to give N-{5-[5-(2,4-dioxo-1,3,8-triazaspiro[4.5]dec-8-yl)pentanoyl]-2,4-dimethoxyphenyl}-4-trifluoromethylbenzenesulfonamide hydrochloride (0.37 g, 0.57 mmol), m.p. 277°–278° C. (dec).

Proceeding similarly as in Example 23 with different starting materials gave the following compounds of Formula I or protected derivatives thereof:

3-methyl-8-[5-oxo-5-(2,4,5-trimethoxyphenyl)pentyl]-1,3,8-triazaspiro[4.5]decane-2,4-dione hydrochloride, m.p. 269°–270° C.;

3-(4-fluorophenyl)propyl-8-[5-oxo-5-(4-chloro-2,6-dimethoxyphenyl)pentyl]-1,3,8-triazaspiro[4.5]decane-2,4-dione hydrochloride, m.p. 233°–235° C.;

8-[5-(4-methoxybiphenyl-3-yl)-5-oxopentyl]-1,3,8-triazaspiro[4.5]decane-2,4-dione hydrochloride, m.p. 198°–200° C.;

8-[5-(2-methoxynaphthalen-1-yl)-5-oxopentyl]-1,3,8-triazaspiro[4.5]decane-2,4-dione hydrochloride, m.p. 162°–173° C.;

8-[5-(5-chloro-2,4-dimethoxyphenyl)5-oxopentyl]-1,3,8-triazaspiro[4.5]decane-2,4-dione hydrochloride, m.p. 164°–166° C.;

8-[6-(5-chloro-2-methoxyphenyl)-6-oxohexyl]-1,3,8-triazaspiro[4.5]decane-2,4-dione hydrochloride, m.p. 144°–148° C.;

8-[5-(5-chloro-2-methoxyphenyl)-5-oxopentyl]-3-methyl-1,3,8-triazaspiro[4.5]decane-2,4-dione hydrochloride, m.p. 260°–263° C.;

3,8-di[5-(5-chloro-2-methoxyphenyl)-5-oxopentyl]-1,3,8-triazaspiro[4.5]decane-2,4-dione maleate, m.p. 122°–123° C.;

8-[5-(2,5-dimethoxyphenyl)-5-oxopentyl]-1,3,8-triazaspiro[4.5]decane-2,4-dione hydrochloride, m.p. 245°–246° C.;

8-[5-(3-methoxynaphthalen-2-yl)-5-oxopentyl]-1,3,8-triazaspiro[4.5]decane-2,4-dione hydrochloride, m.p. 254°–255° C.;

3-tert-butyl-8-[5-(5-chloro-2-methoxyphenyl)-5-oxopentyl]-1-oxa-3,8-diazaspiro[4.5]decane-2-one hydrochloride, m.p. 238°–239° C.;

8-[5-(6-methoxynaphthalen-2-yl)-5-oxopentyl]-1,3,8-triazaspiro[4.5]decane-2,4-dione hydrochloride, m.p. 167° C. (eff);

8-[5-(5-chloro-2-methoxyphenyl)-5-oxopentyl]-1-oxa-3,8-diazaspiro[4.5]decane-2,4-dione hydrochloride, m.p. 168°–178° C.;

8-[5-oxo-5-(2,4,5-trimethoxyphenyl)pentyl]-1,3,8-triazaspiro[4.5]decane-2,4-dione hydrochloride, m.p. 255°–256° C.;

8-[5-(4-amino-5-chloro-2-methoxyphenyl)-5-oxopentyl]-1,3,8-triazaspiro[4.5]decane-2,4-dione hydrochloride, m.p. 167° C.;

8-[5-(3,5-dichloro-2-methoxyphenyl)-5-oxopentyl]-1,3,8-triazaspiro[4.5]decane-2,4-dione hydrochloride, m.p. 219°–220° C.;

8-[5-(5-chloro-2-methoxyphenyl)-5-oxopentyl]-1-phenyl-1,3,8-triazaspiro[4.5]decane-4-one hydrochloride, m.p. 245°–247° C.;

N-(3-{8-[5-(5-chloro-2-methoxyphenyl)-5-oxopentyl]-2,4-dioxo-1,3,8-triazaspiro[4.5]dec-3-yl}propyl-4-methoxybenzenesulfonamide hydrochloride, m.p. 198°–199° C.;

1,3-dimethyl-8-[5-oxo-5-(2,4,5-trimethoxyphenyl)pentyl]-1,3,8-triazaspiro[4.5]decane-2,4-dione hydrochloride, m.p. 245°–246° C.;

8-[5-(4-chloro-2-methoxyphenyl)-5-oxopentyl]-1,3,8-triazaspiro[4.5]decane-2,4-dione hydrochloride, m.p. >130° C.;

8-[5-(2,5-dichlorophenyl)-5-oxopentyl]-1,3,8-triazaspiro[4.5]decane-2,4-dione hydrochloride, m.p. 213°–215° C.;

8-[5-(6-bromo-2-methoxynaphthalen-1-yl)-5-oxopentyl]-1,3,8-triazaspiro[4.5]decane-2,4-dione hydrochloride, m.p. 174°–176° C.;

8-[5-(2-benzyloxy-5-chlorophenyl)-5-oxopentyl]-1,3,8-triazaspiro[4.5]decane-2,4-dione hydrochloride, m.p. 141°–144° C.;

8-[5-(2-methoxy-4,5-methylenedioxyphenyl)-5-oxopentyl]-1,3,8-triazaspiro[4.5]decane-2,4-dione hydrochloride, m.p. 188°–191° C.;

8-[5-(5-chloro-2-ethoxyphenyl)-5-oxopentyl]-1,3,8-triazaspiro[4.5]decane-2,4-dione hydrochloride, m.p. 147° C. (dec);

8-[5-(2-methoxy-5-nitrophenyl)-5-oxopentyl]-1,3,8-triazaspiro[4.5]decane-2,4-dione hydrochloride, m.p. 244°–245° C.;

8-[5-(5-amino-2-methoxyphenyl)-5-oxopentyl]-1,3,8-triazaspiro[4.5]decane-2,4-dione hydrochloride, m.p. >200° C. (dec);

8-[4-(5-chloro-2-methoxyphenyl)-4-oxobutyl]-3-methyl-1,3,8-triazaspiro[4.5]decane-2,4-dione hydrochloride, m.p. 283°–284° C.;

8-[4-(5-chloro-2-methoxyphenyl)-4-oxobutyl]-1,3,8-triazaspiro[4.5]decane-2,4-dione hydrochloride, m.p. 244°–246° C.;

8-[4-(5-chloro-2-hydroxyphenyl)-4-oxobutyl]-1,3,8-triazaspiro[4.5]decane-2,4-dione hydrochloride, m.p. 208°–211° C.;

8-[6-(4-methoxybiphenyl-3-yl)-6-oxohexyl]-3-methyl-1,3,8-triazaspiro[4.5]decane-2,4-dione hydrochloride, m.p. 235°–238° C.;

8-[5-(2-methoxy-5-phenoxyphenyl)-5-oxopentyl]-1,3,8-triazaspiro[4.5]decane-2,4-dione hydrochloride, m.p. 168°–170° C.;

8-[5-(2,4-dimethoxy-5-nitrophenyl)-5-oxopentyl]-1,3,8-triazaspiro[4.5]decane-2,4-dione hydrochloride, m.p. 215°–216° C.;

N-(2-{8-[5-(5-chloro-2-methoxyphenyl)-5-oxopentyl]-2,4-dioxo-1,3,8-triazaspiro[4.5]dec-3-yl}ethyl)methanesulfonamide hydrochloride, m.p. >120° C.;

N-{3-[5-(2,4-dioxo-1,3,8-triazaspiro[4.5]dec-8-yl)pentanoyl]-4-methoxyphenyl}benzamide hydrochloride, m.p. 205°–208° C.;

N-{3-[5-(2,4-dioxo-1,3,8-triazaspiro[4.5]dec-8-yl)pentanoyl]-4-methoxyphenyl}-2-chlorobenzamide hydrochloride, m.p. >170° C.;

N-{4-[2-chloro-5-(2,4-dioxo-3-methyl-1,3,8-triazaspiro[4.5]dec-8-yl)pentanoyl]-5-methoxyphenyl}acetamide hydrochloride, m.p. 182°–184° C.;

N-{3-[5-(2,4-dioxo-1,3,8-triazaspiro[4.5]dec-8-yl)pentanoyl]-4-methoxyphenyl}acetamide hydrochloride, m.p. 249°–250° C.;

N-{3-[5-(2,4-dioxo-1,3,8-triazaspiro[4.5]dec-8-yl)pentanoyl]-4-methoxyphenyl}-4-chlorobenzenesulfonamide hydrochloride, m.p. 215°–218° C.;

8-[5-(2,3-ethylenedioxyphenyl)-5-oxopentyl]-1,3,8-triazaspiro[4.5]decane-2,4-dione hydrochloride, m.p. 170°–175° C. (dec);

8-[5-(5,6-dichloro-2,3-ethylenedioxyphenyl)-5-oxopentyl]-1,3,8-triazaspiro[4.5]decane-2,4-dione hydrochloride, m.p. 282°–284° C. (dec);

N-{5-[5-(2,4-dioxo-1,3,8-triazaspiro[4.5]dec-8-yl)pentanoyl]-2,4-dimethoxyphenyl}benzenesulfonamide hydrochloride, m.p. 191°–193° C.;

8-[5-(5,6-dichloro-2-methoxyphenyl)-5-oxopentyl]-1,3,8-triazaspiro[4.5]decane-2,4-dione hydrochloride, m.p. 167°–170° C.;

N-{5-[5-(2,4-dioxo-1,3,8-triazaspiro[4.5]dec-8-yl)pentanoyl]-2,4-dimethoxyphenyl}naphthalen-1-ylsulfonamide, m.p. 147°–150° C.;

N-{5-[5-(2,4-dioxo-1,3,8-triazaspiro[4.5]dec-8-yl)pentanoyl]-2,4-dimethoxyphenyl}-1-piperidinesulfonamide hydrochloride, m.p. 213°–215° C.;

N-{5-[5-(2,4-dioxo-1,3,8-triazaspiro[4.5]dec-8-yl)pentanoyl]-2,4-dimethoxyphenyl}methanesulfonamide hydrochloride, m.p. 256°–257° C.;

N-{5-[5-(2,4-dioxo-1,3,8-triazaspiro[4.5]dec-8-yl)pentanoyl]-2,4-dimethoxyphenyl}-4-chlorobenzenesulfonamide hydrochloride, m.p. 258°–260° C.;

N-{5-[5-(2,4-dioxo-1,3,8-triazaspiro[4.5]dec-8-yl)pentanoyl]-2,4-dimethoxyphenyl}-4-nitrobenzenesulfonamide hydrochloride, m.p. 261°–262° C.;

N-{5-[5-(2,4-dioxo-1,3,8-triazaspiro[4.5]dec-8-yl)pentanoyl]-2,4-dimethoxyphenyl}-4-toluenesulfonamide hydrochloride, m.p. 266° C.;

N-{5-[5-(2,4-dioxo-1,3,8-triazaspiro[4.5]dec-8-yl)pentanoyl]-2,4-dimethoxyphenyl}-2,4-difluorobenzenesulfonamide hydrochloride, m.p. >170° C. (dec);

N-{5-[5-(2,4-dioxo-1,3,8-triazaspiro[4.5]dec-8-yl)pentanoyl]-2,4-dimethoxyphenyl}-3-chlorobenzenesulfonamide hydrochloride, m.p. 170°–173° C.;

N-{5-[5-(3-(1-methylethyl)-2,4-dioxo-1,3,8-triazaspiro[4.5]dec-8-yl)pentanoyl]-2,4-dimethoxyphenyl}-4-trifluoromethylbenzenesulfonamide hydrochloride, m.p. 205°–206° C.;

N-{5-[5-(3-(2-hydroxyethyl)-2,4-dioxo-1,3,8-triazaspiro[4.5]dec-8-yl)pentanoyl]-2,4-dimethoxyphenyl}-4-trifluoromethylbenzenesulfonamide hydrochloride, m.p. 205°–208° C.;

N-{5-[5-(3-(carboxymethyl)-2,4-dioxo-1,3,8-triazaspiro[4.5]dec-8-yl)pentanoyl]-2,4-dimethoxyphenyl}-4-trifluoromethylbenzenesulfonamide hydrochloride, m.p. >160° C.;

N-{5-[5-(3-(ethoxycarbonylmethyl)-2,4-dioxo-1,3,8-triazaspiro[4.5]dec-8-yl)pentanoyl]-2,4-dimethoxyphenyl}-4-trifluoromethylbenzenesulfonamide hydrochloride, m.p. 153°–157° C.;

(RS)-N-{5-[5-(3-(2,3-dihydroxypropyl)-2,4-dioxo-1,3,8-triazaspiro[4.5]dec-8-yl)pentanoyl]-2,4-dimethoxyphenyl}-4-trifluoromethylbenzenesulfonamide, m.p. 161°–163° C.;

(S)-N-{5-[5-(3-(2,3-dihydroxypropyl)-2,4-dioxo-1,3,8-triazaspiro[4.5]dec-8-yl)pentanoyl]-2,4-dimethoxyphenyl}-4-trifluoromethylbenzenesulfonamide hydrochloride, m.p. 180°–182.5° C., $[\alpha]_D$ +9° (c=0.99, MeOH);

N-{5-[5-(2,4-dioxo-1,3,8-triazaspiro[4.5]dec-8-yl)pentanoyl]-2,4,6-trimethoxyphenyl}-4-trifluoromethylbenzenesulfonamide hydrochloride, m.p. 261°–263° C.;

N-{5-[5-(3-methyl-2,4-dioxo-1,3,8-triazaspiro[4.5]dec-8-yl)pentanoyl]-2,4,6-trimethoxyphenyl}-4-trifluoromethylbenzenesulfonamide hydrochloride, m.p. 190° C.;

N-{5-[5-(3-(4-fluorophenyl)propyl-2,4-dioxo-1,3,8-triazaspiro[4.5]dec-8-yl)pentanoyl]-2,4,6-trimethoxyphenyl}-4-trifluoromethylbenzenesulfonamide hydrochloride, m.p. 205°–207° C.;

1-{5-[5-(2,4-dioxo-1,3,8-triazaspiro[4.5]dec-8-yl)pentanoyl]-2,4-dimethoxyphenyl}-3-(3-trifluoromethylphenyl)urea hydrochloride, m.p. 213° C.;

1-{5-[5-(2,4-dioxo-1,3,8-triazaspiro[4.5]dec-8-yl)pentanoyl]-2,4-dimethoxyphenyl}-3-(4-trifluoromethylphenyl)urea hydrochloride, m.p. 202°–225° C.;

1-{5-[5-(2,4-dioxo-1,3,8-triazaspiro[4.5]dec-8-yl)pentanoyl]-2,4-dimethoxyphenyl}-3-(2-trifluoromethylphenyl)urea hydrochloride, m.p. 200° C. (eff);

1-{5-[5-(2,4-dioxo-1,3,8-triazaspiro[4.5]dec-8-yl)pentanoyl]-2,4-dimethoxyphenyl}-3-prop-2-ylurea hydrochloride, m.p. 190°–198° C. (eff);

N-{5-[5-(2,4-dioxo-1,3,8-triazaspiro[4.5]dec-8-yl)pentanoyl]-2,4-dimethoxyphenyl}-4-trifluoromethoxybenzenesulfonamide hydrochloride, m.p. 265° C. (dec);

N-{5-[5-(2,4-dioxo-1,3,8-triazaspiro[4.5]dec-8-yl)
pentanoyl]-2,4-dimethoxyphenyl}-2-
chlorobenzenesulfonamide hydrochloride, m.p.
174°–200° C.;

N-(4-{5-[5-(2,4-dioxo-1,3,8-triazaspiro[4.5]dec-8-yl)
pentanoyl]-2,4-dimethoxyphenylsulfamoyl}phenyl)
acetamide hydrochloride, m.p. 220°–224° C.;

N-{5-[5-(2,4-dioxo-1,3,8-triazaspiro[4.5]dec-8-yl)
pentanoyl]-2,4-dimethoxyphenyl}-4-prop-2-
ylbenzenesulfonamide hydrochloride, m.p. >280° C.;

N-{5-[5-(2,4-dioxo-1,3,8-triazaspiro[4.5]dec-8-yl)
pentanoyl]-2,4-dimethoxyphenyl}-2-
thiophenesulfonamide hydrochloride, m.p. 169°–171° C.;

N-{5-[5-(2,4-dioxo-1,3,8-triazaspiro[4.5]dec-8-yl)
pentanoyl]-2,4-dimethoxyphenyl}-2-
naphthalenesulfonamide hydrochloride, m.p. 254°–255° C.;

N-{5-[5-(2,4-dioxo-1,3,8-triazaspiro[4.5]dec-8-yl)
pentanoyl]-2,4-dimethoxyphenyl}-5-chloro-2-
thiophenesulfonamide hydrochloride, m.p. 228°–230° C.;

N-{5-[5-(2,4-dioxo-1,3,8-triazaspiro[4.5]dec-8-yl)
pentanoyl]-2,4-dimethoxyphenyl}-4-
methoxybenzenesulfonamide hydrochloride, m.p.
252°–253° C.;

N-{5-[5-(2,4-dioxo-1,3,8-triazaspiro[4.5]dec-8-yl)
pentanoyl]-2,4-dimethoxyphenyl}-4-
pyridinecarboxamide hydrochloride, m.p. 232°–235° C.;

N-{5-[5-(2,4-dioxo-1,3,8-triazaspiro[4.5]dec-8-yl)
pentanoyl]-2,4-dimethoxyphenyl}-2-(5-
trifluoromethylpyrid-2-ylsulfonyl)-4-
thiophenesulfonamide hydrochloride, m.p. 186°–192° C.;

N-{5-[5-(2,4-dioxo-1,3,8-triazaspiro[4.5]dec-8-yl)
pentanoyl]-2,4-dimethoxyphenyl}-5-(5-
trifluoromethylpyrid-2-ylsulfonyl)-2-
thiophenesulfonamide hydrochloride, m.p. 183°–189° C.;

N-{5-[5-(2,4-dioxo-1,3,8-triazaspiro[4.5]dec-8-yl)
pentanoyl]-2,4-dimethoxyphenyl}-3,5-
ditrifluoromethylbenzenesulfonamide hydrochloride,
m.p. 157°–164° C.;

N-{5-[5-(2,4-dioxo-1,3,8-triazaspiro[4.5]dec-8-yl)
pentanoyl]-2,4-dimethoxyphenyl}-5-pyrid-2-yl-2-
thiophenesulfonamide hydrochloride, N-{5-[5-(2,4-dioxo-1,3,8-triazaspiro[4.5]dec-8-yl)
pentanoyl]-2,4-dimethoxyphenyl}-3-
trifluoromethylbenzenesulfonamide hydrochloride, m.p.
178°–181° C.;

N-{5-[5-(2,4-dioxo-1,3,8-triazaspiro[4.5]dec-8-yl)
pentanoyl]-2,4-dimethoxyphenyl}-3,4-
difluorobenzenesulfonamide hydrochloride, m.p.
229°–230° C.;

8-[5-(4-amino-2,5-dimethoxyphenyl)-5-oxopentyl]-1,3,8-
triazaspiro[4.5]decane-2,4-dione hydrochloride, m.p.
182°–190° C.;

8-[7-(5-chloro-2-methoxyphenyl)-7-oxoheptyl]-1,3,8-
triazaspiro[4.5]decane-2,4-dione hydrochloride, m.p.
168°–170° C.;

N-{5-[5-(2,4-dioxo-3-methyl-1,3,8-triazaspiro[4.5]dec-8-
yl)pentanoyl]-2,4-dimethoxyphenyl}-4-
cyanobenzenesulfonamide maleate, m.p. 113°–120° C.;

N-{5-[5-(2,4-dioxo-1,3,8-triazaspiro[4.5]dec-8-yl)
pentanoyl]-2,4-dimethoxyphenyl}-4-
cyanobenzenesulfonamide maleate, m.p. 230°–235° C.;

N-{5-[5-(2,4-dioxo-3-methyl-1,3,8-triazaspiro[4.5]dec-8-
yl)pentanoyl]-2,4-dimethoxyphenyl}-4-
trifluoromethylbenzenesulfonamide hydrochloride, m.p.
181°–182° C.;

N-{5-[6-(2,4-dioxo-1,3,8-triazaspiro[4.5]dec-8-yl)
hexanoyl]-2,4-dimethoxyphenyl}-4-
trifluoromethylbenzenesulfonamide hydrochloride, m.p.
177°–180° C.;

N-{5-[5-(2,4-dioxo-1,3,8-triazaspiro[4.5]dec-8-yl)
pentanoyl]-2,4-dimethoxyphenyl}-4-
trifluoromethylbenzamide hydrochloride, m.p. 245°–248° C.;

8-[5,5-ethylenedioxy-5-(5-chloro-2-methoxyphenyl)pentyl]
-1,3,8-triazaspiro[4.5]decane-2,4-dione, m.p. 154°–155° C.;

N-{5-[5-(2,4-dioxo-1,3,8-triazaspiro[4.5]dec-8-yl)-1,1-
ethylenedioxypentyl]-3,4-ethylenedioxyphenyl}-4-
trifluoromethylbenzenesulfonamide;

8-[4-(5-chloro-2-methoxyphenyl)-4,4-ethylenedioxybutyl]-
1,3,8-triazaspiro[4.5]decane-2,4-dione;

N-{4-[5-(2,4-dioxo-1,3,8-triazaspiro[4.5]dec-8-yl)
pentanoyl]-2,5-dimethoxyphenyl}-4-
chlorobenzenesulfonamide, m.p. >170° C.;

(S)-3-(2,3-dihydroxypropyl)-8-[5-(2-methoxy-5-
phenoxyphenyl)-5-oxopentyl]-1,3,8-triazaspiro[4.5]
decane-2,4-dione hydrochloride, m.p. 194°–196° C. [α]$_D$
+11.2° (c=0.49, MeOH);

N-{5-[5-(3-[2-(hydroxymethyl)-3-hydroxypropyl]-2,4-
dioxo-1,3,8-triazaspiro[4.5]dec-8-yl)pentanoyl]-2,4-
dimethoxyphenyl}-4-
trifluoromethylbenzenesulfonamide, m.p. 223°–226° C.;

8-[5-(2,4-dimethoxyphenyl)-5-oxopentyl]-1,3,8-triazaspiro
[4.5]decane-2,4-dione hydrochloride, m.p. 200°–202° C.;
and 8-[5-(2,4,5-trimethoxyphenyl)-5-oxopentyl]-1,3,8-
triazaspiro[4.5]decane-2,4-dione, m.p. 220°–222° C.

Proceeding similarly, there may be prepared the following compounds of Formula I:

N-{5-[5-(3-(3-hydroxypropyl)-2,4-dioxo-1,3,8-triazaspiro
[4.5]dec-8-yl)pentanoyl]-2,4-dimethoxyphenyl}-4-
trifluoromethylbenzenesulfonamide;

N-{5-[5-(3-[3-(L-valyloxy)propyl]-2,4-dioxo-1,3,8-
triazaspiro[4.5]dec-8-yl)pentanoyl]-2,4-
dimethoxyphenyl}-4-
trifluoromethylbenzenesulfonamide;

N-{5-[5-(3-methoxymethyl-2,4-dioxo-1,3,8-triazaspiro[4.5]
dec-8-yl)pentanoyl]-2,4-dimethoxyphenyl}-4-
trifluoromethylbenzenesulfonamide;

N-{5-[5-(3-acetoxymethyl-2,4-dioxo-1,3,8-triazaspiro[4.5]
dec-8-yl)pentanoyl]-2,4-dimethoxyphenyl}-4-
trifluoromethylbenzenesulfonamide;

N-{5-[5-(1,3-di(methoxymethyl)-2,4-dioxo-1,3,8-
triazaspiro[4.5]dec-8-yl)pentanoyl]-2,4-
dimethoxyphenyl}-4-
trifluoromethylbenzenesulfonamide;

N-{5-[5-(1,3-di.(acetoxymethyl)-2,4-dioxo-1,3,8-
triazaspiro[4.5]dec-8-yl)pentanoyl]-2,4-
dimethoxyphenyl}-4-
trifluoromethylbenzenesulfonamide;

8-[5-(4,6-dimethoxybiphenyl-3-yl)-5-oxopentyl]-1,3,8-
triazaspiro[4.5]decane-2,4-dione; and 3-[2-(hydroxymethyl)-3-hydroxypropyl]-8-[5-(4,6-
dimethoxybiphenyl-3-yl)-5-oxopentyl]-1,3,8-triazaspiro
[4.5]decane-2,4-dione.

EXAMPLE 24

8-[5-(5-Chloro-2-methoxyphenyl)-5-oxopentyl]-1,3,
8-triazaspiro[4.5]decane-2,4-dione The following is the preparation of a compound of Formula I in which n is 4, t is 1., u is 1, X is NH, Y is C(O), Z is C(O), $R^1$ is chloro at the β-position, $R^2$ is methoxy and $R^3$ is hydro.

A mixture of 8-[5,5-ethylenedioxy-5-(5-chloro-2-methoxyphenyl)pentyl]-1,3,8-triaza-spiro[4.5]decane-2,4-dione (1–1.1 g, 2.3–2.6 mmol), prepared as in Example 23, 10% hydrochloric acid (approximately 1 mL) and methanol (approximately 30 mL) was heated to a boil and then allowed to cool and stand approximately 4 hour at 25° C. The solids were collected and dried under vacuum at 70° C. to give 8-[5-(5-chloro-2-methoxyphenyl)-5-oxopentyl]-1,3,8-triazaspiro[4.5]decane-2,4-dione hydrochloride (0.37 g, 0.57 mmol), m.p. 260°–262° C.

Proceeding similarly as in Example 24 with different starting materials gave the following compounds of Formula I:

N-{3-[5-(2,4-dioxo-1,3,8-triazaspiro[4.5]dec-8-yl)pentanoyl]-4,5-ethylenedioxyphenyl}-4-trifluoromethylbenzenesulfonamide hydrochloride, m.p. 261°–262° C.; and 8-[4-(5-chloro-2-methoxyphenyl)-4-oxobutyl]-1-3,8-triaza-spiro[4.5]decane-2,4-dione.

EXAMPLE 25

8-[5-(5-amino-2,4-dimethoxyphenyl)-5-oxopentyl]-1,3,8-triazaspiro[4.5]decane-2,4-dione The following is the preparation of a compound of Formula I in which n is 4, t is 2, u is 1, X is NH, Y is C(O), Z is C(O), $R^1$ is amino and methoxy at the β- and γ-positions, respectively, $R^2$ is methoxy and $R^3$ is hydro.

A mixture of 8-[5-(2,4-dimethoxy-5-nitrophenyl)-5-oxopentyl]-1,3,8-triazaspiro[4.5]decane-2,4-dione (0.33 g, 0.76 mmol), prepared as in Example 23, 10% palladium on carbon (140 mg in 5 mL of water), THF (50 mL) and ethanol (50 mL) was stirred 2 hours under a hydrogen atmosphere (15 psi). The mixture was filtered and concentrated to give 8-[5-(5-amino-2,4-dimethoxyphenyl)-5-oxopentyl]-1,3,8-triazaspiro[4.5]decane-2,4-dione hydrochloride, m.p. 245° C. (dec).

Proceeding similarly as in Example 25 with different starting materials gave the following compounds of Formula I:

8-[5-(5-amino-2-methoxyphenyl)-5-oxopentyl]-1,3,8-triaza-spiro[4.5]decane-2,4-dione, m.p. 211°–213° C.; and N-{5-[5-(2,4-dioxo-1,3,8-triazaspiro[4.5]dec-8-yl)pentanoyl]-2,4-dimethoxyphenyl}-4-aminobenzenesulfonamide hydrochloride, m.p. 206°–208° C.

EXAMPLE 26

1-{5-[5-(2,4-Dioxo-1,3,8-triazaspiro[4.5]dec-8-yl)pentanoyl]-2,4-dimethoxyphenyl}-3-(3-trifluoromethylphenyl)thiourea The following is the preparation of a compound of Formula I in which n is 4, t is 2, u is 1, X is NH, Y is C(O), Z is C(O), $R^1$ is 3-trifluoromethylthioureido and methoxy at the β- and γ-positions, respectively, $R^2$ is methoxy and $R^3$ is hydro.

A mixture of 8-[5-(5-amino-2,4-dimethoxyphenyl)-5-oxopentyl]-1,3,8-triazaspiro[4.5]decane-2,4-dione (62 mg, 0.15 mmol), prepared as in Example 21, α,α,α-trifluoro-m-tolyl isothiocyanate (1.335 g/mL, 0.03 mL, 0.17 mmol) and N-methyl-2-pyrrolidinone was stirred 10 minutes. The mixture was added to water (50 mL) and the solids were collected, washed with water, dried and recrystallized from a solution of hydrogen chloride in ethanol/ether to give 1-{5-[5-(2,4-dioxo-1,3,8-triazaspiro[4.5]dec-8-yl)pentanoyl]-2,4-dimethoxyphenyl}-3-(3-trifluoromethylphenyl)thiourea hydrochloride (40 mg, 0.06 mmol), m.p. 159°–168° C.

EXAMPLE 27

N-{5-[5-(2,4-Dioxo-1,3,8-triazaspiro[4.5]dec-8-yl)pentanoyl]-2,4-dimethoxyphenyl}-3-(5-trifluoromethyl-1-methylpyrazol-3-yl)-2-thiophenesulfonamide The following is the preparation of a compound of Formula I in which n is 4, t is 2, u is 1, X is NH, Y is C(O), Z is C(O), $R^1$ is 3-(5-trifluoromethyl-1-methylpyrazol-3-yl)thien-2-ylsulfonylamino and methoxy at the β- and γ-positions, respectively, $R^2$ is methoxy and $R^3$ is hydro.

A mixture of 8-[5-(5-amino-2,4-dimethoxyphenyl)-5-oxopentyl]-1,3,8-triazaspiro[4.5]decane-2,4-dione (202 mg, 0.5 mmol), prepared as in Example 21, 3-(5-trifluoromethyl-1-methylpyrazol-3-yl)-2-thiophenesulfonyl chloride. (200 mg, 0.6 mmol) and THF (1 mL) and N-methyl-2-pyrrolidinone (1 mL) was stirred 16 hours at approximately 25° C. The mixture was purified by flash chromatography eluting first with methylene chloride and then with methylene chloride/methanol+ammonium hydroxide (9:1). The purified product was recrystallized from ethanol and then from a solution of hydrogen chloride in ethanol/ether to give N-{5-[5-(2,4-dioxo-1,3,8-triazaspiro[4.5]dec-8-yl)pentanoyl]-2,4-dimethoxyphenyl}-3-(5-trifluoromethyl-1-methylpyrazol-3-yl)-2-thiophenesulfonamide hydrochloride (94 mg, 0.13 mmol), m.p. 162°–170° C.

Proceeding similarly as in Example 27 with different starting materials the following compounds of Formula I were prepared:

N-{3-[5-(2,4-dioxo-1,3,8-triazaspiro[4.5]dec-8-yl)pentanoyl]-4-methoxyphenyl}-1-pyrrolidinesulfonamide hydrochloride, m.p. 227°–229° C.;

N-{3-[5-(2,4-dioxo-1,3,8-triazaspiro[4.5]dec-8-yl)pentanoyl]-4-methoxyphenyl}benzenesulfonamide hydrochloride, m.p. 170°–182° C.;

N-{3-[5-(2,4-dioxo-1,3,8-triazaspiro[4.5]dec-8-yl)pentanoyl]-4-methoxyphenyl}-3,4-dimethoxybenzenesulfonamide hydrochloride, m.p. 150°–167° C.; and 4-{5-[5-(2,4-dioxo-1,3,8-triazaspiro[4.5]dec-8-yl)pentanoyl]-2,4-dimethoxyphenylsulfamoyl}benzenesulfonamide, m.p. 270°–272° C.

EXAMPLE 28

8-[5-(5-Chloro-2-methoxyphenyl)-5-oxopentyl]-1-oxa-3,8-diazaspiro[4.5]decane-2-one The following is the preparation of a compound of Formula I in which n is 1, t is 1, u is 1, X is. O, Y is CH, Z is C(O), $R^1$ is chloro at the β-position, $R^2$ is methoxy and $R^3$ is hydro.

A mixture of 3-tert-butyl-8-[5-(5-chloro-2-methoxyphenyl)-5-oxopentyl]-1-oxa-3,8-triazaspiro[4.5]decane-2-one (200 mg, 0.46 mmol), prepared as in Example 23, trifluoroacetic acid (5 mL) and water (2 mL) was heated 6 days at reflux and then concentrated to 2 mL: The residue was combined with water and the mixture was treated with sodium bicarbonate and then extracted with methylene chloride. The product was purified by column chromatography eluting with methylenechloride/methanol+ammonium hydroxide (20:1) to give 8-[5-(5-chloro-2-methoxyphenyl)-5-oxopentyl]-1-oxa-3,8-triazaspiro[4.5]decane-2-one (50 mg, 0.13 mmol). The free base was recrystallized from a solution of hydrogen chloride in ethanol/ether to give 8-[5-(5-chloro-2-methoxyphenyl)-5-oxopentyl]-1-oxa-3,8-triazaspiro[4.5]decane-2-one hydrochloride, m.p. 130°–134° C.

EXAMPLE 29

The following are representative pharmaceutical formulations containing a compound of Formula I.

ORAL FORMULATION

A representative solution for oral administration contains:

| | |
|---|---|
| Compound of Formula I | 100–1000 mg |
| Citric Acid Monohydrate | 105 mg |
| Sodium Hydroxide | 18 mg |
| Flavoring | |
| Water | q.s. to 100 mL |

INTRAVENOUS FORMULATION

A representative solution for intravenous administration contains:

| | |
|---|---|
| Compound of Formula I | 10–100 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

TABLET FORMULATION

A representative tablet form of a compound of Formula I may contain:

| | |
|---|---|
| Compound of Formula I | 1% |
| Microcrystalline Cellulose | 73% |
| Stearic Acid | 25% |
| Colloidal Silica | 1%. |

EXAMPLE 30

Cloned Rat 5-HT$_{2C}$ Receptor Binding Assay

The following describes an in vitro binding assay utilizing cloned 5-HT$_{2C}$ receptors radiolabelled with [$^3$H] mesulergine.

Mouse NIH3T3 fibroblasts expressing a cloned rat 5-HT$_{2C}$ receptor were maintained in Dulbecco's Modified Eagle medium with 10% Fetal Calf Serum and g/mL G418 in 95/5% O$_2$/CO$_2$. The cells were harvested using 2 mM EDTA in phosphate buffered saline (calcium/magnesium free) and centrifuged (500 g). The cell pellet was homogenized using a Polytron P10 disrupter (setting 5, 5 sec) in homogenization buffer (Tris, 50 mM; Na$_2$EDTA, 5 mM) and the homogenate was centrifuged at 19,500 rpm using a Sorvall/Dupont RC5C centrifuge with an SS34 rotor (30,000–48,000 g, 15 minutes). The pellet was homogenized (setting 5, 5 sec) in homogenization buffer and the homogenate was centrifuged (30,000–48,000 g, 15 minutes). The pellet was homogenized (setting 5, 5 sec) in resuspension buffer (Tris, 50 mM; EDTA 0.5 mM) and the homogenate was centrifuged (30,000–48,000 g, 15 minutes). The pellet was homogenized (setting 5, 5 sec) in a small volume of resuspension buffer to give approximately 1×10$^7$ cells/mL. The membranes were separated into 1 mL aliquots and stored at −70° C.

The membranes were thawed at room temperature and diluted with assay buffer (NaCl, 118 mM; KCl, 4.5 mM; KH$_2$PO$_4$, 1.2 mM; CaCl$_2$.2H$_2$O, 2.5 mM; MgCl$_2$, 1 mM; D-glucosel 10 mM; Tris, 25 mM). An optimal dilution ratio was predetermined for each batch of membranes to ensure that less than 10% of 5×10$^{-10}$M [$^3$H]mesulergine binds, specific binding is at least 10. times greater than a machine background of 23 dpm and the best ratio of specific binding to total binding is achieved. The membranes were homogenized (setting 5, 5 sec) and then added to assay tubes containing mesulergine (5×10$^{-10}$M), test compound (1×10$^{-10}$–1×10$^{-4}$M) and assay buffer (q.s. to 500 μL). The assay mixture was incubated at 32° C. for 60 minutes and then filtered over 0.1% polyethyleneimine pretreated glass fiber filtermats using a Brandel cell harvester. The assay tubes were rinsed with cold 0.1M sodium chloride (3× 3 sec) and dried by drawing air over the filter for 10 seconds. Radioactivity retained on the filters was determined by liquid scintillation counting. In a similar fashion, total binding was measured with methysergide (1×10$^{-5}$M) in the absence of test compound. For each compound tested the concentration producing 50% inhibition of binding (IC$_{50}$) was determined using iterative curve fitting techniques.

Proceeding as in Example 30, compounds of the invention were tested and found to have affinity for the 5-HT$_{2C}$ receptor.

EXAMPLE 31

Cloned Rat 5-HT$_{2C}$ Receptor Functional Assay

The following describes an in vitro functional assay utilizing 5-HT induced, 5-HT$_{2C}$ mediated increases in NIH3T3 cellular metabolic activity.

Mouse NIH3T3 fibroblasts expressing cloned 5-HT$_{2C}$ receptor were maintained in high glucose Dulbecco's Minimal Essential Medium (DMEM) further comprising glutamine, sodium pyruvate and 10% Fetal Bovine. The cells were harvested using 2 mM EDTA in phosphate buffered saline and transferred to 6.5 mm transwell capsule plates (3 micron pore size) to give approximately 1×10$^5$ cells/capsule. The cells were allowed to adhere overnight and then transwell spacers and inserts were added to each transwell capsule. The capsules were placed into sensor chambers and the sensor chambers were loaded onto a microphysiometer.

The 5-HT$_{2C}$ receptor antagonist properties of test compounds were appraised by determining their affect on 5-HT induced increases in cellular metabolic activity, expressed as percent increase in acidification rate. Microphysiometer Running Medium (high glucose, sodium bicarbonate free DMEM) was pump through the transwell capsules for 1.5 minutes, 30 seconds of which 5-HT was present in the medium, followed by a 45 minute washout and recovery period. In this manner, cells were exposed to 5-HT in a non-cumulative concentration fashion, increasing in concentration until maximal or near maximal effect was observed.

Concentration-effect curves were constructed for 5-HT with and without the test compound present. Data was analyzed by iterative curve fitting techniques and the concentration ratio (CR) of 5-HT necessary to produce equiactive responses in the absence and presence of the test compound was determined. Relying on the concentration ratio, the molar concentration of the test compound, and the relationship:

$$pK_b = -\log \frac{[\text{test compound}]}{CR - 1}$$

the negative log of the dissociation constant ($pK_b$) for each test compound was determined.

Proceeding as in Example 31, compounds of the invention were tested and found to be antagonists at the 5-HT$_{2C}$ receptor.

EXAMPLE 32

Anxiolytic Behavior Assay

The following describes an in vivo method for determining anxiolytic activity by measuring the extent the drug affects the natural anxiety of mice when exposed to a novel, brightly lighted environment.

Naive male C5BI/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolytic behavior is seen as a general increase in exploratory activity in the lighted area. An increase in exploratory activity is reflected by increased latency (the time for the mouse to move to the dark chamber when first placed in the center of the lighted area), increase in shuttle activity, increased or unaltered locomotor activity (number of grid lines crossed) and decreased time spent in the dark compartment.

EXAMPLE 33

Withdrawal Anxiety Assay

The following describes an in vivo procedure for determining amelioration of the symptoms caused by withdrawal from addictive substances by measuring the extent the drug affects the anxiety that occurs in mice after chronically treating with an addictive substance and then abruptly ceasing the treatments.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 14). Anxiolysis is seen as a general increase in exploratory activity in the lighted area. An increase in exploratory activity is reflected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0 % w/v in drinking water), nicotine (0.1 mg/kg, i.p., twice daily) or cocaine (1.0 mg/kg; i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawal phase by intraperitoneal injection. Responses are represented as inhibition of the decrease in anxiolytic behavior after the ethanol, cocaine or nicotine treatment is ceased.

We claim:

1. A compound of the formula:

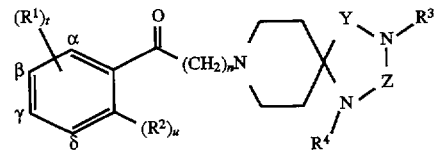

in which:

n is 2, 3, 4, 5 or 6;

t is 1, 2, 3 or 4;

u is 0 or 1 (provided that t is not 1 when u is 0);

Y and Z are independently C(O), C(S) or CH$_2$ (provided that Y and Z are not both CH$_2$);

each R$^1$ is independently: amino, carbamoyl, cyano, halo, nitro, thiocarbamoyl, thioureido, ureido, a group selected from (C$_{1-4}$)alkyl, (C$_{1-4}$)alkyloxy, or (C$_{1-4}$) alkylthio (optionally further substituted with one to three halo atoms), a group selected from aryloxy, aryl(C$_{1-4}$)alkyloxy, arylsulfonyl, or arylthio, a group selected from —NHSO$_2$R$^5$, —NHC(O)R$^5$, —NHC(O) NHR$^5$, —NHC(S)NHR$^5$ and —SO$_2$NHR$^5$ {which R$^5$ is (C$_{1-4}$)alkyl (optionally further substituted with one to three halo atoms) or a group selected from aryl, aryl (C$_{1-4}$)alkyl, heteroaryl and heteroaryl (C$_{1-4}$)alkyl (optionally further substituted with one to two radicals independently selected from amino, carbamoyl, cyano, halo, nitro, a group selected from (C$_{1-4}$)alkanoyl, (C$_{1-4}$)alkylsulfonylamino, (C$_{1-4}$)alkanoylamino, (C$_{1-4}$)alkyl and (C$_{1-4}$)alkyloxy, optionally further substituted with one to three halo atoms, and a group selected from aryl, arylsulfonyl, heteroaryl and heteroarylsulfonyl, optionally further substituted with one to two radicals independently selected from amino, cyano, halo, nitro and a group selected from (C$_{1-4}$)alkyl and (C$_{1-4}$)alkyloxy, optionally further substituted with one to three halo atoms)} or with an adjacent R$^1$ radical form ethylenedioxy, methylenedioxy or butadienylene (the butadienylene being optionally substituted with one or two radicals selected from halo and (C$_{1-4}$) alkyloxy);

R² is hydroxy, halo, (C₁₋₄)alkyloxy, phenyl (C₁₋₄)alkyloxy or naphthyl (C₁₋₄)alkyloxy;

R³ is H, (C₁₋₆)alkyl (optionally substituted with a group selected from —C(O)OH, —C(O)O(C₁₋₄)alkyl, —NHSO₂R⁵ and —NHC(O)R⁵, in which R⁵ is as defined above), hydroxyalkyl, esterified hydroxyalkyl, —CH₂O(C₁₋₄)alkyl, —CH₂OC(O)(C₁₋₄)alkyl, phenyl (C₁₋₄)alkyl (optionally substituted with one or two radicals independently selected from amino, cyano, halo, hydroxy, nitro, trifluoromethyl, trifluoromethoxy, acetamido, methanesulfonamido, (C₁₋₄)alkyl, or (C₁₋₄)alkyloxy), or a group of Formula (a):

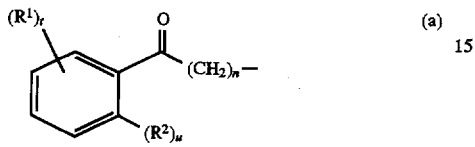

in which n, t, u, R¹, and R² are as defined above; and

R⁴ is H, (C₁₋₄)alkyl, or aryl, or R⁴ and R⁵ are the same and are both —CH₂O(C₁₋₄)alkyl or —CH₂OC(O)(C₁₋₄)alkyl;

or a pharmaceutically acceptable salt or N-oxide thereof, where the term "aryl" denotes phenyl or naphthyl;

the term "heteroaryl" denotes thienyl, furyl, pyrrolyl, imidazolyl, or pyridinyl;

the term "hydroxyalkyl" denotes a straight or branched monovalent hydrocarbon radical of two to four carbon atoms, substituted with one or two hydroxy groups, provided that (1) the carbon bonded to the nitrogen is unsubstituted with hydroxy, and (2) if two hydroxy groups are present, they are not both on the same carbon atom; and the term "esterified hydroxyalkyl" denotes "hydroxyalkyl" as defined above in which the hydroxy group (if only one is present) or both hydroxy groups (if two are present) are esterified with a (C₁₋₄)alkanoic acid or a neutral naturally-occurring α-amino acid.

2. A compound of claim 1 in which:

n is 3, 4, 5 or 6;

t is 2 or 3;

u is 0;

Y is C(O);

Z is C(O) or C(S);

two adjacent R¹ radicals form α,β-ethylenedioxy, and a third R¹, when present, is amino, halo, nitro, ureido, thioureido, (C₁₋₄)alkyloxy, phenoxy, or a group selected from —NHSO₂R⁵, —NHC(O)R⁵, —NHC(O)NHR⁵ and —NHC(S)NHR⁵ {which R⁵ is (C₁₋₄)alkyl, phenyl, naphthyl, or thienyl (the phenyl, naphthyl, or thienyl being optionally further substituted with one to two radicals independently selected from amino, carbamoyl, cyano, halo, nitro, a group selected from (C₁₋₄)alkanoyl, (C₁₋₄)alkylsulfonylamino, (C₁₋₄)alkanoylamino, (C₁₋₄)alkyl and (C₁₋₄)alkyloxy, optionally further substituted with one to three halo atoms)};

R³ is H, (C₁₋₆)alkyl (optionally substituted with a group selected from —C(O)OH, —C(O)O(C₁₋₄)alkyl, —NHSO₂R⁵ and —NHC(O)R⁵, in which R⁵ is as defined above), hydroxyalkyl, esterified hydroxyalkyl, or phenyl (C₁₋₄)alkyl (the phenyl being optionally substituted with one or two radicals independently selected from amino, cyano, halo, hydroxy, nitro, trifluoromethyl, trifluoromethoxy, acetamido, methanesulfonamido, (C₁₋₄)alkyl, or (C₁₋₄)alkyloxy); and R⁴ is H.

3. A compound of claim 1 in which:

n is 3, 4, 5 or 6;

t is 1, 2 or 3;

u is 1;

Y is C(O);

Z is C(O) or C(S);

R¹ is amino, phenoxy, halo, nitro, ureido, thioureido, (C₁₋₄)alkyloxy, a group selected from —NHSO₂R⁵, —NHC(O)R⁵, —NHC(O)NHR⁵ and —NHC(S)NHR⁵ {which R⁵ is (C₁₋₄)alkyl or a group selected from phenyl, naphthyl, or thienyl (the phenyl, naphthyl, or thienyl being optionally substituted with one to two radicals independently selected from amino, carbamoyl, cyano, halo, nitro, a group selected from (C₁₋₄)alkanoyl, (C₁₋₄)alkylsulfonylamino, (C₁₋₄)alkanoylamino, (C₁₋₄)alkyl and (C₁₋₄)alkyloxy, optionally further substituted with one to three halo atoms)} or with an adjacent R¹ radical forms butadienylene (the butadienylene being optionally further substituted with one or two radicals selected from halo or (C₁₋₄)alkyloxy);

R² is (C₁₋₄)alkyloxy;

R³ is H, (C₁₋₆)alkyl (optionally substituted with a group selected from —C(O)OH, —C(O)O(C₁₋₄)alkyl, —NHSO₂R⁵ and —NHC(O)R⁵, in which R⁵ is as defined above), hydroxyalkyl, esterified hydroxyalkyl, or phenyl (C₁₋₄)alkyl (the phenyl being optionally substituted with one or two radicals independently selected from amino, cyano, halo, hydroxy, nitro, trifluoromethyl, trifluoromethoxy, acetamido, methanesulfonamido, (C₁₋₄)alkyl, or (C₁₋₄)alkyloxy); and R⁴ is H.

4. A compound of claim 3 in which:

n is 4, 5 or 6;

t is 1, 2, or 3;

an R¹ is attached at the β-position and is amino, phenoxy, chloro, nitro, (C₁₋₄)alkyloxy or —NHSO₂R⁵ {which R⁵ is phenyl or thienyl (the phenyl or thienyl being optionally substituted with amino, carbamoyl, cyano, chloro, fluoro, nitro or a group selected from (C₁₋₄)alkanoyl, (C₁₋₄)alkylsulfonylamino, (C₁₋₄)alkanoylamino, (C₁₋₄)alkyl and (C₁₋₄)alkyloxy, optionally further substituted with one to three fluoro atoms)} or is attached at the γ-position and is chloro, (C₁₋₄)alkyloxy, or amino; and R² is methoxy.

5. A compound of claim 4 in which:

n is 4;

t is 2;

Z is C(O);

an R¹ is attached at the β-position and is phenylsulfonylamino (optionally substituted with amino, carbamoyl, cyano, chloro, fluoro, nitro or a group selected from (C₁₋₄)alkanoyl, (C₁₋₄)alkylsulfonylamino, (C₁₋₄)alkanoylamino, (C₁₋₄)alkyl and (C₁₋₄)alkyloxy, optionally further substituted with one to three fluoro atoms), and an R¹ is attached at the γ-position and is methoxy.

6. A compound of claim 5 in which:

the R$^1$ at the β-position is 4-trifluoromethylphenylsulfonylamino.

7. A compound of claim 6 in which:

R$^3$ is H, (C$_{1-6}$)alkyl, hydroxyalkyl, esterified hydroxyalkyl, or phenyl (C$_{1-4}$)alkyl {where the phenyl is optionally substituted with halo, hydroxy, (C$_{1-4}$) alkyloxy, or trifluoromethyl}.

8. The compound of claim 7 which is N-{5-[5-(2,4-dioxo-1,3,8-triazaspiro[4.5]dec-8-yl)pentanoyl]-2,4-dimethoxyphenyl}-4-trifluoromethylbenzenesulfonamide or a pharmaceutically acceptable salt thereof.

9. The compound of claim 7 which is N-{5-[5-(2,4-dioxo-3-methyl-1,3,8-triazaspiro[4.5]dec-8-yl)pentanoyl]-2,4-dimethoxyphenyl}-4-trifluoromethylbenzenesulfonamide or a pharmaceutically acceptable salt thereof.

10. A compound of claim 4 in which:

n is 4;

t is 2;

Z is C(O);

an R$^1$ is attached at the γ-position and is chloro; and an R$^1$ is attached at the α-position and is methoxy.

11. A compound of claim 10 in which:

R$^3$ is H, (C$_{1-6}$)alkyl, hydroxyalkyl, esterified hydroxyalkyl, or phenyl (C$_{1-4}$)alkyl {where the phenyl is optionally substituted with halo, hydroxy, (C$_{1-4}$) alkyloxy, or trifluoromethyl}.

12. The compound of claim 11 which is 8-[5-(4-chloro-2,6-dimethoxyphenyl)-5-oxopentyl]-3-(3-(4-fluorophenyl)propyl)-1,3,8-triazaspiro[4.5]decane-2,4-dione or a pharmaceutically acceptable salt thereof.

13. A compound of claim 6 in which:

n is 4;

t is 3;

Z is C(O); and an R$^1$ is attached at the β-position and is phenylsulfonylamino (optionally substituted with amino, carbamoyl, cyano, chloro, fluoro, nitro or a group selected from (C$_{1-4}$)alkanoyl, (C$_{1-4}$)alkylsulfonylamino, (C$_{1-4}$) alkanoylamino, (C$_{1-4}$)alkyl and (C$_{1-4}$)alkyloxy, optionally further substituted with one to three fluoro atoms), an R$^1$ is attached at the α-position and is methoxy, and an R$^1$ is attached at the γ-position and is methoxy.

14. A compound of claim 13 in which:

the R$^1$ at the β-position is 4-trifluoromethylphenylsulfonylamino.

15. A compound of claim 14 in which:

R$^3$ is H, (C$_{1-6}$)alkyl, hydroxyalkyl, esterified hydroxyalkyl, or phenyl (C$_{1-4}$)alkyl {where the phenyl is optionally substituted with halo, hydroxy, (C$_{1-4}$) alkyloxy, or trifluoromethyl}.

16. The compound of claim 15 which is N-{5-[5-(2,4-dioxo-1,3,8-triaza-spiro[4.5]dec-8-yl)pentanoyl]-2,4,6-trimethoxyphenyl}-4-trifluoromethylbenzenesulfonamide or a pharmaceutically acceptable salt thereof.

17. The compound of claim 16 which is N-{5-[5-(2,4-dioxo-3-methyl-1,3,8-triaza-spiro[4.5]dec-5-yl)pentanoyl]-2,4,6-trimethoxyphenyl}-4-trifluoromethylbenzenesulfonamide or a pharmaceutically acceptable salt thereof.

* * * * *

UNITED STATES PATENT AND TRADEMARK OFFICE
CERTIFICATE OF CORRECTION

PATENT NO. : 5,739,336
DATED : Apr. 14, 1998
INVENTOR(S) : Weinhardt et al.

It is certified that error appears in the above-indentified patent and that said Letters Patent is hereby corrected as shown below:

Claim 1, column 53, line 21 "$R^S$" should read --$R^3$--.

Claim 3, column 54, line 15 "$R^S$" should read --$R^5$--.

Claim 17, column 56, line 29 "dec-5-yl" should read --dec-8-yl--.

Signed and Sealed this

Thirtieth Day of June, 1998

*Attest:*

BRUCE LEHMAN

*Attesting Officer*   *Commissioner of Patents and Trademarks*